(12) United States Patent
Shibata

(10) Patent No.: US 9,005,916 B2
(45) Date of Patent: Apr. 14, 2015

(54) BLOOD CELL ANALYZER, BLOOD CELL ANALYZING METHOD, AND NON-TRANSITORY STORAGE MEDIUM

(71) Applicant: Sysmex Corporation, Kobe-shi (JP)

(72) Inventor: Masaharu Shibata, Kobe (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 0 days.

(21) Appl. No.: 13/729,751

(22) Filed: Dec. 28, 2012

(65) Prior Publication Data

US 2013/0171681 A1 Jul. 4, 2013

(30) Foreign Application Priority Data

Dec. 28, 2011 (JP) .................. 2011-289445

(51) Int. Cl.
*G01N 1/10* (2006.01)
*G01N 35/10* (2006.01)
*G01N 35/00* (2006.01)
*G01N 15/14* (2006.01)

(52) U.S. Cl.
CPC *G01N 1/10* (2013.01); *G01N 35/10* (2013.01); *G01N 35/1016* (2013.01); *G01N 35/0092* (2013.01); *G01N 2035/00465* (2013.01); *G01N 2015/1486* (2013.01); *G01N 35/00603* (2013.01)

(58) Field of Classification Search
CPC ............ G01N 2035/0465; G01N 35/0092; G01N 35/01016
See application file for complete search history.

(56) References Cited

U.S. PATENT DOCUMENTS

| | | |
|---|---|---|
| 2004/0023404 A1 | 2/2004 | Shibata |
| 2007/0048868 A1* | 3/2007 | Shibata et al. ................. 436/43 |
| 2008/0131898 A1 | 6/2008 | Tsuji et al. |
| 2008/0241957 A1 | 10/2008 | Shibata et al. |
| 2010/0112703 A1* | 5/2010 | Tanaka ............................ 436/47 |
| 2010/0248293 A1 | 9/2010 | Kuwano et al. |

FOREIGN PATENT DOCUMENTS

| | | |
|---|---|---|
| CN | 101852797 A | 10/2010 |
| JP | 62-226059 A | 10/1987 |
| JP | 11-101798 A | 4/1999 |
| JP | 2006-292732 A | 10/2006 |

* cited by examiner

*Primary Examiner* — P. Kathryn Wright

(74) *Attorney, Agent, or Firm* — Brinks Gilson & Lione

(57) ABSTRACT

The present invention is a blood cell analyzer. When only measuring one or more measurement items included in one group, a first sample supplying operation is performed which includes aspirating a blood sample by a first amount. When measuring one or more measurement items included in the one group and another measurement item not included in the one group, a second sample supplying operation and a third sample supplying operation are performed. The second sample supplying operation includes aspirating the blood sample by the first amount for the measurement items included in the one group, and the third sample supplying operation includes aspirating the blood sample by a second amount for the another measurement item.

18 Claims, 14 Drawing Sheets

| | SAMPLE NO. | OUTPUT | P/N | ACTION | ORDER TYPE | ERROR | DATE | TIME | Seq. | DATE RECEIVED |
|---|---|---|---|---|---|---|---|---|---|---|
| LW | LW Sample 02 M | DGH | | Review | Manual | | 2010/08/06 | 07:09:51 | 8 | 2010/08/06 07:09:51 |
| LW | 12345678901234567890 1 M | DGH | | Review | Manual | | 2010/08/06 | 07:09:51 | 8 | 2010/08/06 07:09:51 |
| LW | 12345678901234567890 1 A | DGH | | Review | Manual | | 2010/08/06 | 07:08:34 | 7 | 2010/08/06 07:08:34 |
| LW | LW Sample 01 M | DGH | | Review | Manual | | 2010/08/06 | 07:08:34 | 7 | 2010/08/06 07:08:34 |
| BF | BACKGROUNDCHECK A | DGH | | | Manual | | 2010/08/06 | 07:08:34 | 6 | 2010/08/06 07:08:34 |
| WB | BACKGROUNDCHECK A | DGH | | | Manual | | 2010/08/06 | 07:06:32 | 6 | 2010/08/06 07:06:32 |
| PD | PD Sample 03 M | DGH | | | Manual | | 2010/08/06 | 07:05:43 | 10 | 2010/08/06 07:05:43 |
| PD | 12345678901234567890 1 B | DGH | | | Manual | | 2010/08/06 | 06:55:06 | 10 | 2010/08/06 06:55:06 |
| PD | 12345678901234567890 1 C | DGH | | | Manual | | 2010/08/06 | 06:49:23 | 9 | 2010/08/06 06:49:23 |
| PD | PD Sample 02 M | DGH | | | Manual | | 2010/08/06 | 06:49:23 | 9 | 2010/08/06 06:49:23 |
| WB | Sample 11 M | DGH | | | Manual | | 2010/08/06 | 06:46:22 | 8 | 2010/08/06 06:46:22 |
| WB | 12345678901234567890 1 M | DGH | | | Manual | | 2010/08/06 | 06:44:49 | 7 | 2010/08/06 06:44:49 |
| WB | Sample 10 M | DGH | | | Manual | | 2010/08/06 | 06:44:49 | 7 | 2010/08/06 06:44:49 |
| WB | Sample 9 M | DGH | | | Manual | | 2010/08/06 | 06:43:22 | 6 | 2010/08/06 06:43:22 |
| WB | Sample 8 M | DGH | | | Manual | | 2010/08/06 | 06:41:51 | 5 | 2010/08/06 06:41:51 |
| WB | Sample 7 M | DGH | | | Manual | | 2010/08/06 | 06:39:59 | 4 | 2010/08/06 06:39:59 |
| WB | BACKGROUNDCHECK A | DGH | | | Manual | | 2010/08/06 | 06:37:53 | 3 | 2010/08/06 06:37:53 |
| BF | BF Sample 02 M | DGH | | | Manual | | 2010/08/06 | 06:31:14 | 14 | 2010/08/06 06:31:14 |

FILTER: FILTER 01 DATE [2010/05/05 TO 2020/08/08]
SORT: MEASUREMENT DATE/TIME (DESCENDING)

| ITEM | | UNIT |
|---|---|---|
| BC | 175 | 10^4/uL |
| GB | 5.3 | g/dL |
| CT | 16.5 | % |
| CV | 94.3 | fL |
| CH | 30.3 | pg |
| CHC | 32.1 | g/dL |
| LT& | 11.0 | 10^4/uL |
| DW-SD | 40.5 | fL |
| DW-CV | 11.9 | % |
| DW | 13.4 | fL |
| PV | 11.7 | fL |
| -LCR | 38.9 | % |
| CT | 0.10 | % |
| RBC# | 0.0* | 10^2/uL |
| RBC% | 0.0* | % |
| EUT# | 20.5* | 10^2/uL |
| YMPH# | 7.6* | 10^2/uL |
| ONO# | 2.9* | 10^2/uL |
| O# | 1.1* | 10^2/uL |
| ASO# | 0.1* | 10^2/uL |
| EUT% | 63.7* | % |
| YMPH% | 23.6* | % |
| ONO% | 9.0* | % |
| O% | 3.4* | % |
| ASO% | 0.3* | % |
| ET% | 1.29 | % |
| ET# | 2.26 | 10^4/uL |
| RF | 7.7 | % |
| FR | 92.3 | % |
| FR | 6.1 | % |
| FR | 1.6 | % |
| HPC# | 123.45 | 10^2/uL |

SAMPLE INFO | CBC | DIFF | RET | PLT-F

BLOOD CELL ANALYZER, BLOOD CELL ANALYZING METHOD, AND NON-TRANSITORY STORAGE MEDIUM

RELATED APPLICATIONS

This application claims priority under 35 U.S.C. §119 to Japanese Patent Application No. 2011-289445 filed on Dec. 28, 2011, the entire content of which is hereby incorporated by reference.

FIELD OF THE INVENTION

The present invention relates to a blood cell analyzer, blood cell analyzing method, and non-transitory storage medium for analyzing blood samples collected from humans or animals.

BACKGROUND OF THE INVENTION

Blood sample analyzers for analyzing blood samples collected from humans and animals are known.

The blood cell analyzers aspirate a blood sample from a sample container that holds a blood sample, prepare a measurement sample from the aspirated blood sample and reagent, and measure the measurement sample in a measurement section to obtain measurement results.

Japanese Laid-Open Patent Publication No. 2006/292732 discloses a blood cell analyzer capable of measuring the number of red blood cells, number of white blood cells, and hemoglobin. This blood cell analyzer is preloaded with a liquid in the aspirating tube, and is configured to aspirate a blood sample into the aspirating tube with an air gap (layer of air) formed at the tip of the aspirating tube. The blood sample aspirated into the aspirating tube is slightly diluted by the residual liquid remaining on the inner wall of the aspirating tube in conjunction with the movement within the tube despite contact being prevented between the blood sample and the liquid within the aspirating tube by the air gap. Hence, the concentration of the blood sample disposed at the base end side of the aspirating tube is slightly lower compared to the concentration of the blood sample disposed at the tip end side of the aspirating tube, and a slight concentration gradient is produced in the blood sample within the aspirating tube.

U.S. Patent Application Publication No. 2010/248293 discloses a blood cell analyzer capable of performing classification measurements of white blood cells, measurement of reticulocytes, and measurement of nucleated red blood cells in addition to measurements of the number of red blood cells, number of white blood cells, and hemoglobin. This blood cell analyzer is configured to obtain measurement order of specified measurement items, calculate the amount of blood sample needed for the measurement according to the measurement item specified in the measurement order, aspirate the calculated amount of blood sample from the sample container, and execute the measurements of each measurement item.

The blood cell analyzer disclosed in Japanese Laid-Open Patent Publication No. 2006/292732 is configured to measure each sample for predetermined measurement items and aspirate a fixed amount of blood sample into the aspirating tube for each measurement, therefore sample aspiration conditions for each measurement is identical. Therefore, the concentration gradient of the blood sample within the aspirating tube, for example, is the same for each measurement. In this blood cell analyzer, blood samples diluted to the same degree are used in identical measurement items for any measurement since which part of a blood sample in the aspirating tube to use for a measurement item is determined beforehand. The measurement results are therefore unaffected by the concentration gradient produced in the blood sample within the aspirating tube.

On the other hand, when the blood cell analyzer disclosed in Japanese Laid-Open Patent Publication No. 2006/292732 is configured to change the type and number of measurement items for each sample similar to the blood cell analyzer of U.S. Patent Application Publication No. 2010/248293, it is necessary to aspirate an amount of sample capable of supporting all measurement items even when, for example, only measuring a single measurement item since a fixed amount of blood sample must be aspirated whatever measurement is to be performed in order to have identical aspiration conditions for each sample (blood sample).

When the blood cell analyzer disclosed in Japanese Laid-Open Patent Publication No. 2006/292732 is configured to change the type and number of measurement items for each sample, there is concern of some fluctuation in the concentration gradient of the sample within the aspirating tube for each sample due to the difference in the amount of aspirated sample in each measurement when only the required amount of sample needed for the measurement is aspirated, as in the case of the blood cell analyzer of US Patent Application Publication No. 2010/248293. Therefore, when an equal part of the sample of the aspirating tube is used in identical measurement items for each measurement, there will be a slight difference in the degree of dilution of the sample in each measurement, which causes concern that the measurement results will be affected.

Note that washing liquid remains on the inner wall of the aspirating tube and sampling valve because the aspirating tube and the sampling valve are washed each measurement even when aspirating a blood sample that does not fill the interior of the aspirating tube as in blood analyzers that measure blood samples using the sampling valve. There is therefore concern of some variation of the blood sample concentration gradient among measurements when different amounts of sample are aspirated for each measurement. Common measurement items are preferably performed under identical sample aspiration conditions for each measurement.

SUMMARY OF THE INVENTION

The scope of the present invention is defined solely by the appended claims, and is not affected to any degree by the statements within this summary.

A first aspect of the present invention is a blood cell analyzer, comprising: a sample aspirating section which comprises an aspiration tube for aspirating a blood sample, and which aspirates a blood sample from a sample container by using the aspiration tube; a sample preparing section configured to prepare a measurement sample from the blood sample aspirated by the sample aspirating section and a reagent; a measuring section configured to measure the measurement sample prepared by the sample preparing section; and an information processing section configured to: control the sample aspirating section so as to perform a first sample supplying operation when the information processing section has received an instruction to only measure one or more measurement items included in one group with respect to the blood sample, wherein the first sample supplying operation includes aspirating the blood sample by a first amount and supplying the aspirated blood sample to the sample preparing section; and control the sample aspirating section so as to perform a second sample supplying operation and a third sample supplying operation when the information processing section has received an instruction to measure one or more measurement items included in the one group and another measurement item not included in the one group with respect to the blood sample, wherein the second sample supplying operation includes aspirating the blood sample by the first amount for the measurement items included in the one group and supplying the aspirated blood sample to the sample preparing section, and the third sample supplying operation includes aspirating the blood sample by a second amount for the another measurement item and supplying the aspirated blood sample to the sample preparing section.

A second aspect of the present invention is a blood cell analyzing method, comprising: a step of receiving an instruction of a measurement item with respect to a blood sample; a step of aspirating the blood sample in a sample container using an aspirating tube, and supplying the aspirated blood sample to a sample preparing section to prepare a measurement sample to be used in a measurement; a step of preparing the measurement sample from a reagent and the blood sample supplied to the sample preparing section; and a step of measuring the prepared measurement sample, wherein when an instruction has been received to only measure one or more measurement items included in one group in the receiving step, a first sample supplying operation is performed in the supplying step, wherein the first sample supplying operation comprises an operation of aspirating the blood sample by a first amount and an operation of supplying the aspirated blood sample to the sample preparing section; and when an instruction has been received to measure one or more measurement items included in the one group and another measurement item not included in the one group in the receiving step, a second sample supplying operation and a third sample supplying operation are performed in the supplying step, wherein the second sample supplying operation comprises an operation of aspirating the blood sample by the first amount for the measurement items included in the one group and an operation of supplying the aspirated blood sample to the sample preparing section, and the third sample supplying operation comprises an operation of aspirating the blood sample by a second amount for the another measurement item and an operation of supplying the aspirated blood sample to the sample preparing section.

A third aspect of the present invention is at least one non-transitory storage medium which stores programs executable collectively by at least one processor to perform processes comprising: receiving an instruction of a measurement item with respect to a blood sample; and controlling a sample aspirating section to aspirate a blood sample in a sample container using an aspirating tube, and supplying the aspirated blood sample to a sample preparing section, wherein the processor controls the sample aspirating section so as to perform a first sample supplying operation when an instruction has been received to only measure one or more measurement items included in one group with respect to the blood sample, wherein the first sample supplying operation comprises an operation of aspirating the blood sample by a first amount and an operation of supplying the aspirated blood sample to the sample preparing section; and the processor controls the sample aspirating section so as to perform a second sample supplying operation and a third sample supplying operation when an instruction has been received to measure one or more measurement items included in the one group and another measurement item not included in the one group with respect to the blood sample, wherein the second sample supplying operation comprises an operation of aspirating the blood sample by the first amount for the measurement items included in the one group and an operation of supplying the aspirated sample to the sample preparing section, and the third sample supplying operation comprises an operation of aspirating the blood sample by a second amount for the another measurement item and an operation of supplying the aspirated sample to the sample preparing section.

A fourth aspect of the present invention is a blood cell analyzer with a first measurement mode, and a second measurement mode for measuring another measurement item in addition to a measurement item that is measured in the first measurement mode, the blood cell analyzer comprising: a sample aspirating section which comprises an aspiration tube for aspirating a blood sample, and which aspirates a blood sample from a sample container by using the aspiration tube; a sample preparing section configured to prepare a measurement sample from the blood sample aspirated by the sample aspirating section and a reagent; a measuring section configured to measure the measurement sample prepared by the sample preparing section; and an information processing section configured to: control the sample aspirating section so as to perform a first sample supplying operation in the first measurement mode, the first sample supplying operation comprises an operation of aspirating the blood sample by a first amount for one or more measurement items selected from one group having a plurality of measurement items, and an operation of supplying the aspirated blood sample to the sample preparing section; and control the sample aspirating section so as to perform a second sample supplying operation and a third sample supplying operation in the second measurement mode, wherein the second sample supplying operation comprises an operation of aspirating the blood sample by the first amount for one or more measurement items included in the one group, and an operation of supplying the aspirated blood sample to the sample preparing section, and the third sample supplying operation comprises an operation of aspirating the blood sample by a second amount for another measurement item that are not included in the one group, and an operation of supplying the aspirated blood sample to the sample preparing section.

BRIEF DESCRIPTION OF THE DRAWINGS

FIG. 11 shows an example of the analysis result list screen of the blood cell analyzer of the embodiment;

FIG. 12 shows another example of the analysis results list screen of the blood cell analyzer of the embodiment;

DETAILED DESCRIPTION OF THE PREFERRED EMBODIMENT

The preferred embodiments of the present invention are described hereinafter with reference to the drawings.

First Embodiment

[Structure of the Blood Cell Analyzer]

Figure 1:
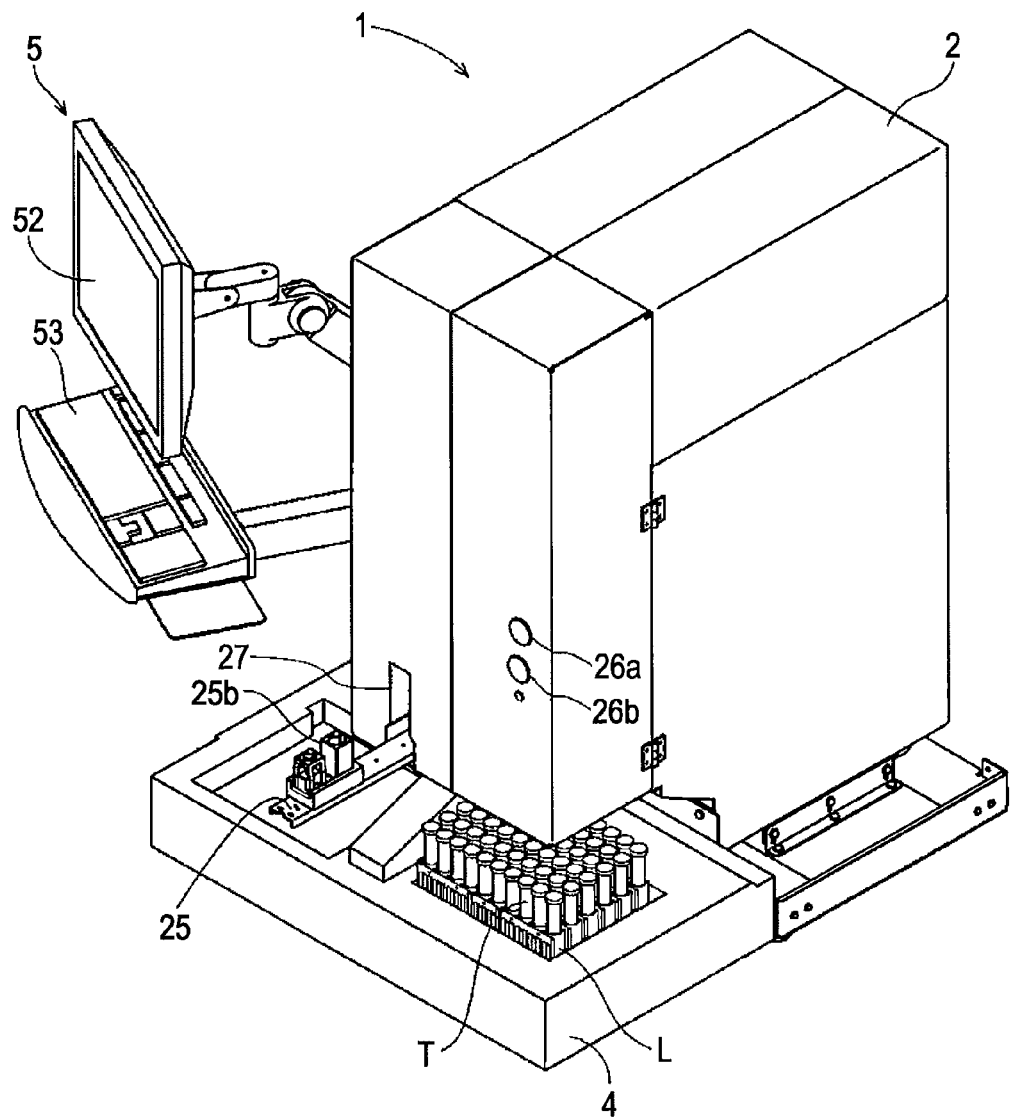
FIG. 1 is a perspective view showing the general structure of an embodiment of the blood cell sample analyzer.

FIG. 1 is a perspective view showing the general structure of an embodiment of the blood cell analyzer. The blood cell analyzer 1 of the present embodiment is a multi-item blood cell analyzer for detecting and counting each white blood cell, red blood cell, platelets and the like contained in a blood sample. As shown in FIG. 1, the blood cell analyzer 1 is configured by a measurement unit 2, transporting unit 4 disposed on the front side of the measurement unit 2, and information processing unit 5 for controlling the measurement unit 2 and the transporting unit 4.

The front surface of the measurement unit 2 is provided with a mode switch 26a which the user uses to switch the measurement mode (manual measurement mode and sampler measurement mode, details of which are described later), and a measurement start switch 26b which the user uses to start the measurement of a blood sample. When the mode switch 26a is pressed, the operation mode is switched from the default measurement mode, that is, the sampler measurement mode, to the manual measurement mode, and the sample container transporter 25 moves the sample container T from the take-up port 27 (described later) into the measurement unit 2. When the user loads the sample container (blood collection tube) T that contains the blood sample to be measured into the sample container transporter 25 and presses the measurement start switch 26b, the sample container T is taken into the measurement unit 2 together with the sample container transporter 25. The measurement unit 2 aspirates the blood sample from the sample container T, and starts the measurement of the blood sample. The sample container T is tube-like and has an open top end. A blood sample collected from a patient is contained within the sample container T, and the open top end of the sample container T is sealed by a cap. The sample container T is configured of light-transmitting glass or synthetic resin, and the blood sample is visible within the container. A barcode label is adhered to the side surface of the sample container T. A barcode representing the sample ID is printed on the barcode label.

<Structure of Measuring Unit 2>

Figure 2:
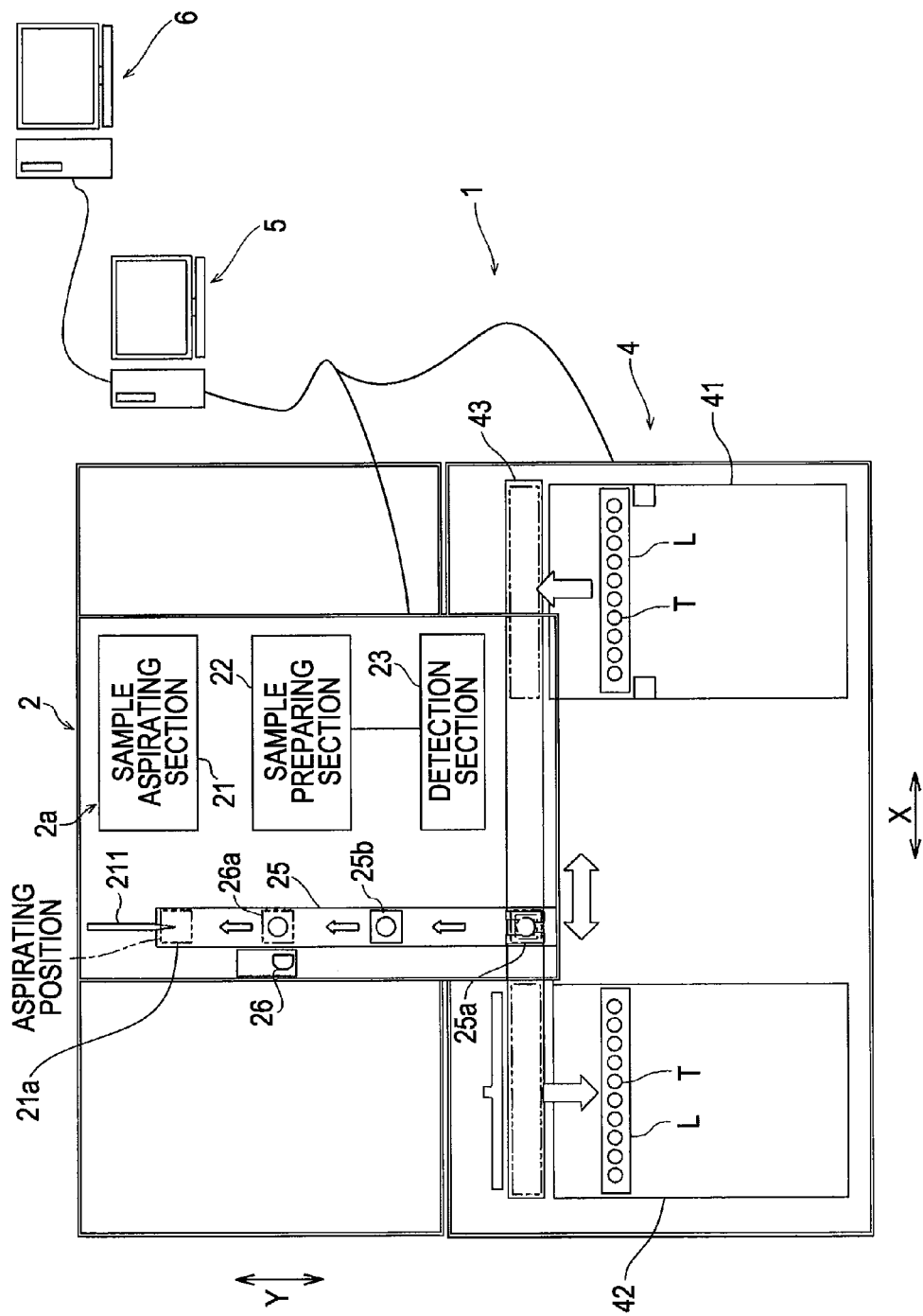
FIG. 2 is a block diagram showing the structure of the measurement unit provided in the blood cell analyzer of the embodiment.

The structure of the measurement unit is described below. FIG. 2 is a block diagram showing the structure of the measurement unit 2. As shown in FIG. 2, the measurement unit 2 has a measurement device 2a that incorporates a sample aspirating section 21 for aspirating blood from a sample container T, a sample preparing section 22 for preparing a measurement sample for use in measurements from the blood aspirated by the sample aspirating section 21, and a detection section 23 for detecting blood cells from the measurement sample prepared by the sample preparing section 22. The measurement unit 2 also has a take-up port for taking a sample container T held in a sample rack L moved by the rack transporter 43 of the transporting unit 4 into the measurement unit 2, and a sample container transporter 25 for taking the sample container T from the rack L into the measurement unit 2 and moving the sample container T to an aspirating position of the sample aspirating section 21.

The structure of the sample container transporter 25 will be described first. The sample container transporter 25 is provided with a sample container receiver 25b that has a hole for inserting a sample container T. The sample container T is placed in the sample container receiver 25b by the user. The sample container receiver 25b is horizontally movable in the Y direction via the motive force of a step motor that is not shown in the drawing.

A barcode reader 26 is provided within the measurement unit 2. The sample container receiver 25b is movable to a barcode reading position 26a near the barcode reader 26, and an aspirating position 21a of the sample aspirating section 21. When the sample container receiver 25b is moved to the barcode reading position 26a, the sample barcode is read by the barcode reader 26. When the sample container receiver 25b is moved to the aspirating position, the blood sample is aspirated from held the sample container T by the sample aspirating section 21.

Figure 3:
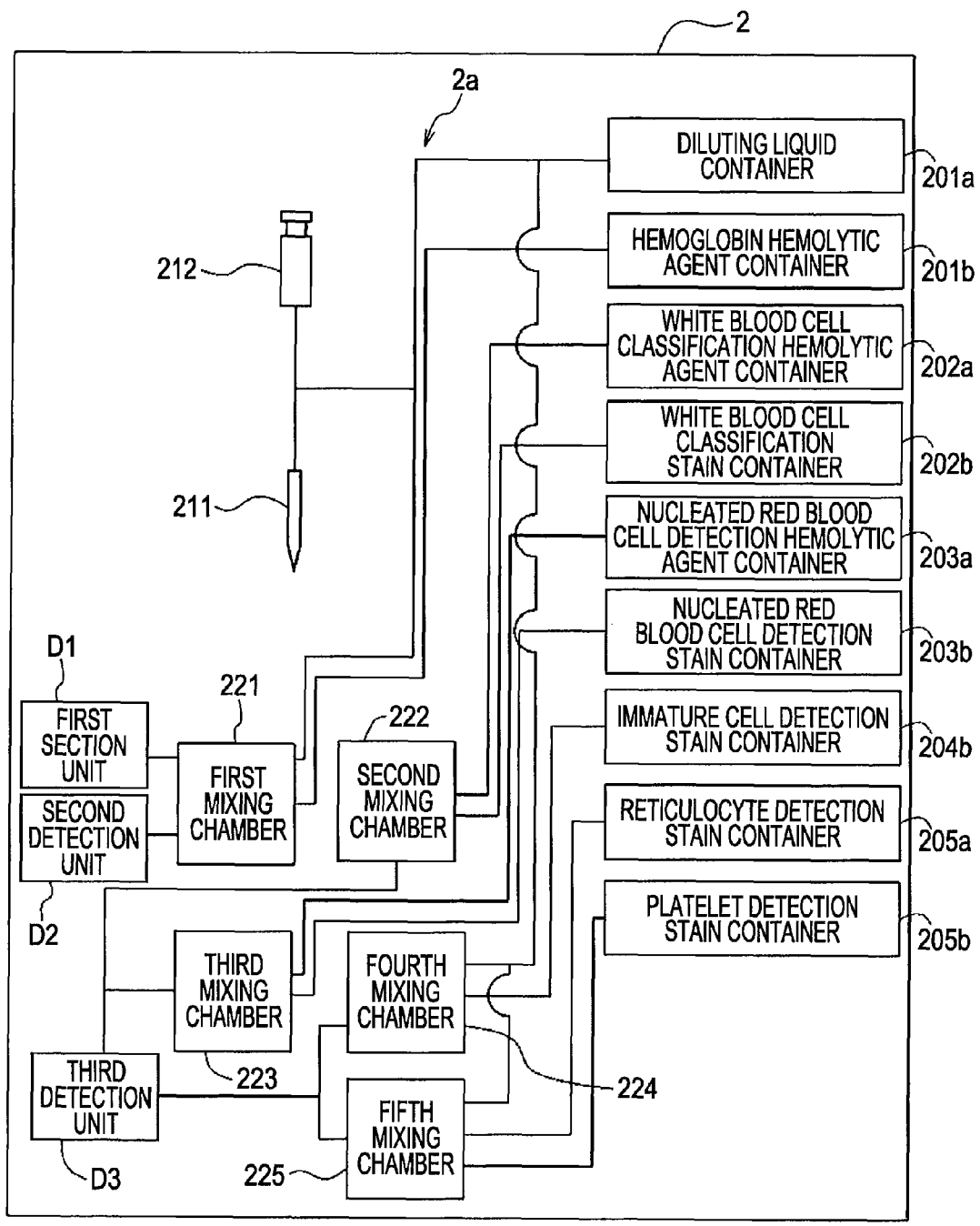
FIG. 3 is a schematic view showing the structure of the measuring device in the measurement unit.

FIG. 3 is a schematic view showing the structure of the measuring device in the measurement unit 2. As shown in FIGS. 2 and 3, an aspirating tube 211 is provided at the tip of the sample aspirating section 21. A syringe pump 212 is connected to the aspirating tube 211 through a tube. The sample aspirating section 21 is movable in vertical directions so that the aspirating tube 211 pierces the cap of the sample container T via a downward movement when the sample container T has moved to the aspirating position. Before aspirating the blood sample, the sample aspirating section 21 is controlled so as to fill the tube and interior of the aspirating tube 211 with diluting liquid, and further controlled so as to form an air layer at the tip of the aspirating tube 211. The blood sample within the sample container T is aspirated by the aspirating tube 21 by driving the syringe pump 212 to move the diluting liquid in the tube and within the aspirating tube 21.

The sample preparing section 22 is provided with five chambers including a first mixing chamber 221, second mixing chamber 222, third mixing chamber 223, fourth mixing chamber 224, and fifth mixing chamber 225. The blood sample aspirated from the sample container T by the aspirating tube 211 is supplied to any chamber among the first mixing chamber 221, second mixing chamber 222, third mixing chamber 223, fourth mixing chamber 224, and fifth mixing chamber 225.

A reagent container accommodating reagent may be placed in the measurement unit 2, and the reagent container may be connected to a flow path. Specifically, the reagent containers used in the present embodiment are a diluting liquid container 201a containing diluting liquid (washing liquid), hemoglobin hemolytic agent container 201b containing hemoglobin hemolytic agent, white blood cell classification hemolytic agent container 202a containing white blood cell classification hemolytic agent for dissolving red blood cells, white blood cell classification stain container 202b containing white blood cell classification stain for staining white blood cells, nucleated red blood cell detection hemolytic agent container 203a containing hemolytic agent for detecting white blood cells and nucleated red blood cells, nucleated red blood cell detection stain container 203b containing stain used for detecting white blood cells and nucleated red blood cells, immature cell detection stain container 204b containing stain used for detecting immature cells such as myeloblasts and abnormal lymphoid cells, reticulocyte detection stain container 205a containing stain used for detecting reticulocytes, and platelet detection stain container 205b containing stain for detecting platelets. Note that a prepared aqueous solution having a near neutral normal pH (̂ to 8) and osmotic pressure near isotonic (240 to 330 Osm/kg) is suitable as diluting liquid to maintain cell morphology.

The diluting liquid container 201a and the hemoglobin hemolytic agent container 201b are connected to the first mixing chamber 221 through tubes so as to respectively be capable of supplying diluting liquid and hemoglobin hemolytic agent to the first mixing chamber 221 via a diaphragm pump.

The white blood cell classification hemolytic agent container 202a and the white blood cell classification stain container 202b are connected to the second mixing chamber 222 through tubes, so as to respectively be capable of supplying white blood cell classification hemolytic agent and white blood cell classification stain to the second mixing chamber 222 via a diaphragm pump.

The nucleated red blood cell classification hemolytic agent container 203a and the nucleated red blood cell classification stain container 203b are connected to the third mixing chamber 223 through tubes, so as to respectively be capable of supplying nucleated red blood cell classification hemolytic agent and nucleated red blood cell classification stain to the second mixing chamber 223 via a diaphragm pump.

The diluting liquid container 201a and the immature cell detection stain container 204b are connected to the fourth mixing chamber 224 through tubes so as to respectively be capable of supplying diluting liquid and immature cell detection stain to the fourth mixing chamber 224 via a diaphragm pump.

The diluting liquid container 201a, the reticulocyte detection stain container 205a, and the platelet detection stain container 205b are connected to the fifth mixing chamber 225 through tubes so as to respectively be capable of supplying diluting liquid, reticulocyte detection stain, and platelet detection stain to the fifth mixing chamber 225 via a diaphragm pump.

The detection section 23 is provided with a first detection unit D1 for performing measurements related to red blood cells and platelets, a second detection unit D2 for performing measurements related to hemoglobin, and a third detection unit D3 for performing measurements related to white blood cells.

The first mixing chamber 221 is the site for preparing RBC/PLT measurement samples used in the analyses of red blood cells and platelets, and HGB measurement samples used in analyses of hemoglobin. The RBC/PLT measurement sample prepared in the first mixing chamber 221 is used for measurements (hereinafter referred to as "RBC/PLT measurements") performed by the first detection unit D1, and the HGB measurement sample is used for measurements (hereinafter referred to as "HGB measurements") performed by the second detection unit D2.

The second mixing chamber 222 is the site for preparing DIFF measurement samples used in white blood cell classification. The DIFF measurement samples prepared in the second mixing chamber 222 are used in the white blood cell classification measurements performed by the third detection unit D3.

The third mixing chamber 223 is the site for preparing WNR measurement samples used in the detection of white blood cells and nucleated red blood cells. The WNR measurement samples prepared in the third mixing chamber 223 are used in measurements (hereinafter referred to as "WNR measurements") of white blood cells and nucleated red blood cells performed by the third detection unit D3.

The fourth mixing chamber 224 is the site for preparing WPC measurement samples used in the detection of immature cells, and HPC measurement samples used in the detection of hematopoietic progenitor cells. The WPC measurement samples prepared in the fourth mixing chamber 224 are used in measurements (hereinafter referred to as "WPC measurements") of immature cells performed by the third detection unit D3, and the HPC measurement samples prepared in the fourth mixing chamber 224 are used in measurements (hereinafter referred to as "HPC measurements") of hematopoietic progenitor cells.

The fifth mixing chamber 225 is the site for preparing RET measurement samples used in the detection of reticulocytes, and PLT-F measurement samples used in the optical measurements of platelets. The RET measurement samples prepared in the fifth mixing chamber 225 are used in measurements (hereinafter referred to as "RET measurements") of reticulocytes performed by the third detection unit D3, and the PLT-F measurement samples are used in the optical measurements (hereinafter referred to as "PLT-F measurements") of platelets performed by the third detection unit D3.

The first detection unit D1 is configured as a RBC/PLT detection unit for performing RBC measurements (measure red blood cell count), and PLT measurements (measure platelet count). The RBC/PLT detection unit D1 measures RBC and PLT using a sheath flow detection method.

The second detection unit D2 is configured as an HGB detection unit to perform HGB measurements (measure hemoglobin content in the blood). The HGB detection unit D2 measures HGB using the SLS-Hemoglobin method.

The third detection unit D3 is configured as an optical detection unit capable of performing WNR, white blood cell classification, WPC, HPC, and RET measurements. WNR measurements detect WBC (white blood cells) and NRBC (nucleated red blood cells); white blood cell classification measurements detect NEUT (neutrophils), LYMPH (lymphocytes), EO (eosinophils), and MONO (monocytes); WPC measurements detect immature myeloblasts (BLAST) and abnormal lymphocytes; HPC measurements detect HPC (hematopoietic progenitor cells); RET measurements detect RET (reticulocytes); and PLT-F measurements detect PLT-F (platelets). The third detection unit D3 performs each measurement using a semiconductor laser and a flow cytometric method. The information processing unit 5 analyzes the measurement data obtained through each type of measurement.

The third detection unit D3 has a flow cell; the third detection unit D3 irradiates a measurement sample moving through the flow cell by semiconductor laser light, receives the produced forward scattered light, side scattered light and fluorescent light, and detects the intensities of the forward scattered light, side scattered light, and fluorescent light. Measurement data, which includes the optical information of the obtained intensities of the forward scattered light, side scattered light, and fluorescent light, are transmitted from the measurement unit 2 to the information processing unit 5, and the received measurement data are then analyzed by the information processing unit 5.

<Structure of Transporting Unit>

The structure of the transporting unit 4 is described below. As shown in FIG. 1, the transporting unit 4 is arranged in front of the measurement unit 2 of the blood cell analyzer 1. The transporting unit 4 is capable of moving a rack L holding a plurality of sample containers T to supply blood samples to the measurement unit 2.

As shown in FIG. 2, the transporting unit 4 is configured by a pre-analysis rack holder 41 capable of temporarily holding a plurality of racks L that accommodate sample containers T containing a blood sample to be analyzed, post-analysis rack holder 42 capable of temporarily holding a plurality of racks L that accommodate blood sample containers T from which the blood sample has been aspirated by the measurement unit 2, and rack transporter 43 for moving the rack L received from the pre-analysis rack holder 41 to the post-analysis rack holder 42 after analysis by moving the rack L in a linear horizontal direction of arrow X in the drawing to supply the blood sample to the measurement unit 2. The blood cell analyzer 1 not only performs measurement operations in the manual measurement mode wherein the user manually places a sample container T on the sample container transport 25, but also performs measurement operations in the sampler measurement mode wherein the rack L is moved by the transporting unit 4 and the sample container is automatically taken from the moved rack L into the measurement unit 4. In the sampler measurement mode, a rack L placed on the pre-analysis rack holder 41 is moved in the X direction by a rack transporter 43, and the blood sample is aspirated from the sample container held in the rack L at the aspirating position and measured by the measurement unit 2. When the blood sample is aspirated from all sample containers held in the rack L, the rack L is moved to the post-analysis rack holder 42.

Note that only the measurement operation performed in the manual measurement mode is described below.

<Structure of Information Processing Unit>

Figure 4:
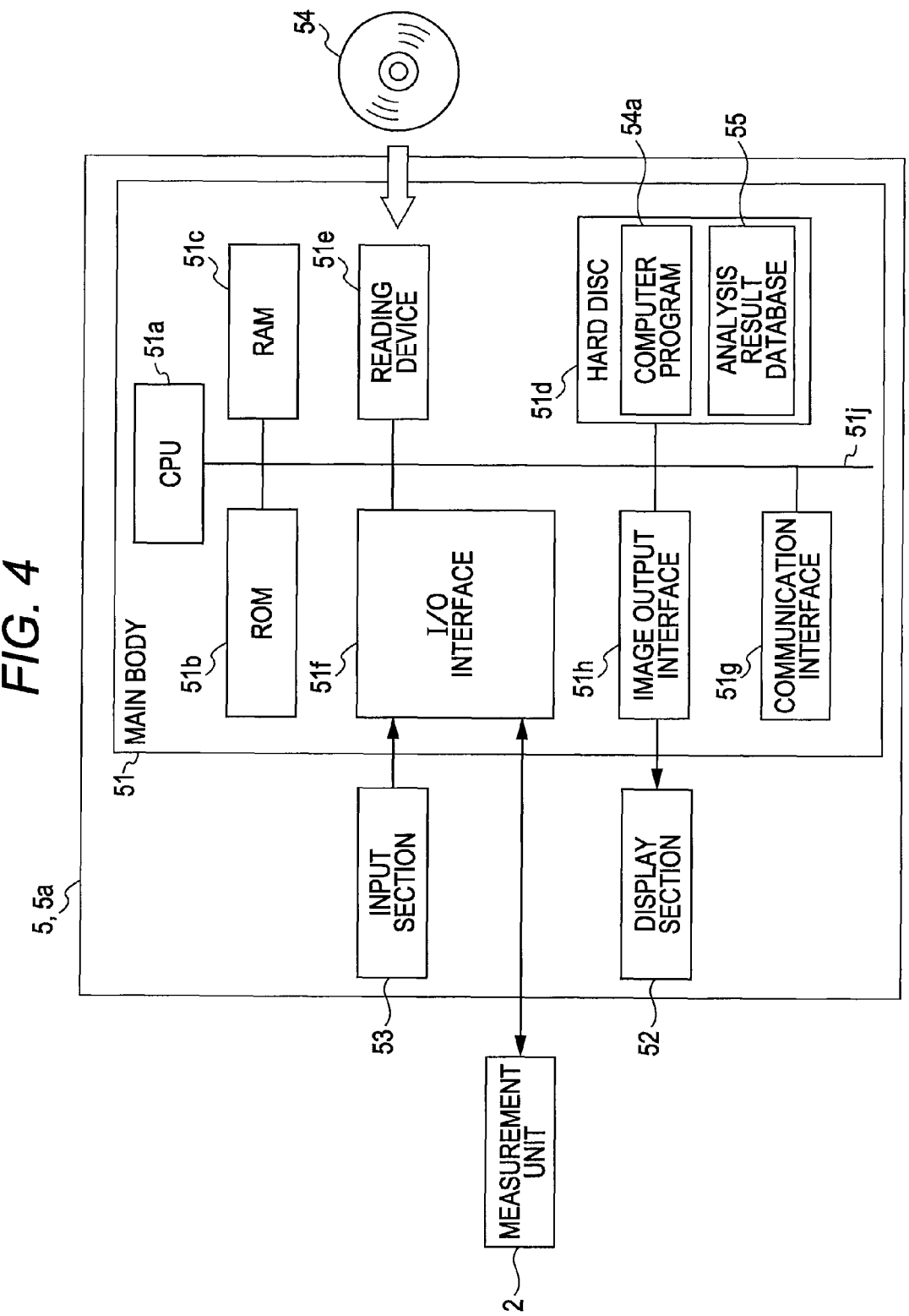
FIG. 4 is a block diagram showing the structure of the information processing unit provided in the blood cell analyzer of the embodiment.

The structure of the information processing unit 5 is described below. The information processing unit 5 is configured by a computer. FIG. 4 is a block diagram showing the structure of the information processing unit 5. As shown in FIG. 4, a computer 5a is provided with a main body 51, display section 52, and input section 53. The main body 51 is provided with a CPU 51a, ROM 51b, RAM 51c, hard disk 51d, reading device 51e, I/O interface 51f, communication interface 51g, and image output interface 51h; the CPU 51a, ROM 51b, RAM 51c, hard disk 51d, reading device 51e, I/O interface 51f, communication interface 51g, and image output interface 51h are connected by a bus 51j.

The CPU 51a is capable of executing a computer program loaded in the RAM 51c. the computer 5a functions as the information processing unit 5 when the CPU 51a executes computer programs for sample analysis and controlling the measurement unit 2 and transporting unit 4 (described later).

The ROM 51b is configured by a mask ROM, PROM, EPROM, EEPROM or the like, and is used to store computer programs to be executed by the CPU 51a and data used in the execution of such computer programs.

The RAM 51c is configured by SRAM. DRAM or the like. The RAM 51c is used when reading a computer program 54a stored on the hard disk 51d. The RAM 51c is used as a work area of the CPU 51a when the CPU 51a executes computer programs.

The hard disk 51d holds various installed computer programs that are executed by the CPU 51a, including an operating system and application programs, as well as the data used when executing these computer programs. The computer program 54a (to be described later) is also installed on the hard disk 51d. The computer program 54a is an event driven computer program.

The hard disk 51d is provided with an analysis result database 55 for storing the sample analysis results obtained by the blood cell analyzer 1. The analysis result database 55 stores analysis result information that includes patient ID for identifying the patient from whom the blood sample was collected, patient name, diagnosis of the patient, patient attribute information such as principal treatment and the like, blood sample ID (sample number), and measurement information such as day of measurement, time of measurement, measured value, and anomaly information obtained when an abnormality is detected in a blood sample.

The reading device 51e is configured by a floppy disk drive, CD-ROM drive, DVD-ROM drive or the like, and is capable of reading computer programs or data recorded on a portable recording medium 54. Computer program 54a is stored on the portable recording medium 54, and the application program 54a can be read from the portable recording medium 54 by a computer 5a so as to be installed on the hard disk 51d.

Note that the application program 54a can be provided not only by the portable recording medium 54, but also can be provided via an electrical communication line from an external device that is capable of communicating with the computer over the electrical communication line (landline or wireless). For example, the application program 54a may be stored on the hard disk of a server computer on a network, such that the computer 5a can access the server computer to download the application program 54a which is then installed on the hard disk 51d.

A multitasking operating system such as, for example, Microsoft Windows (registered trademark) is also installed on the hard disk 51d. In the following description, the computer program 54a of the present embodiment operates in the environment of such an operating system.

The I/O interface 51f is configured by a serial interface such as, for example, USB, IEEE 1394, RS-232 or the like, parallel interface such as SCSI, IDE, IEEE 1284 or the like, or analog interface such as D/A converter, A/D converter or the like. The input section 53 configured by a keyboard and mouse is connected to the I/O interface 51f, and data may be input to the computer 5a through the I/O interface 51f by using the input section 51f. The input section 53 configured by a keyboard and mouse is connected to the I/O interface 51f, and data can be input to the computer 51a by the operator using the input section 53. Hence, the information processing unit 5 is capable of controlling the measurement unit 2 and the transporting unit 4, respectively.

The communication interface 51g is an Ethernet (registered trademark) interface. The communication interface 51g is connected to a host computer through a LAN that is not shown in the drawings. The computer 5a transmits and receives data to/from the host computer connected to the LAN via the communication interface 51g using a predetermined communication protocol.

The image output interface 51h is connected to the display section 52 configured by an LCD or CRT or the like, so that image signals corresponding to image data received from the CPU 51a are output to the display section 52. The display section 52 displays images (screens) based on the input image signals.

The blood cell analyzer 1 of the present embodiment receives measurement orders in the information processing unit 5. A measurement order for each blood sample is input by the user operating the input section 53 of the information processing unit 5. The user may also input a measurement order to a clinical examination information managing apparatus 6 (refer to FIG. 2) connected to the blood sample analyzer 1 so as to be capable of communication. In this case, the measurement order is transmitted from the clinical examination information managing apparatus 6 to the information processing unit 5. The input measurement order is stored on the hard disk 51d, and used in measurement operations. The blood cell analyzer 1 is capable of analyzing blood samples for measurement items such as the previously mentioned RBC, PLT, HGB, WBC, NRBC, NEUT, LYMPH, EO, MONO, BLAST, HPC, RET, PLT-F and the like. In the blood cell analyzer 1, a measurement item group that includes one or more measurement items is determined beforehand, and measurement orders specifying this measurement item group are receivable. The measurement item group may be a complete blood count measurement item (CBC), white blood cell classification item (DIFF), reticulocyte measurement item (RET), platelet measurement item (PLT-F), immature blood cell measurement item (WPC), and hematopoietic progenitor cell measurement item (HPC). The complete blood count measurement is frequently performed when examining for patient blood diagnosis, long-term observation, anemia, infection, and hemorrhage; and at the very least a red blood cell count, white blood cell count, amount of hemoglobin, hematocrit value, mean corpuscular volume, mean corpuscular hemoglobin, mean corpuscular hemoglobin concentration, and platelet count, are calculated. The CBC measurement item group includes RBC, PLT, HGB, WBC and the like; the DIFF measurement item group includes NEUT, LYMPH, EO, MONO, BASO and the like; the RET measurement item group includes RET; the PLT-F measurement item group includes PLT-F; the WPC measurement item group includes BLAST and the like; the HPC measurement item group includes HPC as well as the items of CBC, DIFF, RET, and PLT-F groups. For example, when a measurement order specifying the CBC measurement item group is input, blood sample measurements are performed for RBC, PLT, HGB, WBC measurement items which are included in the CBC measurement item group; when a measurement order specifying the HPC measurement item group is input, blood sample measurements are performed for HPC measurement items included in the HPC measurement item group and RBC, PLT-F, HGB, WBC, NEUT, LYMPH, EO, MONO, RET, PLT-F measurement items which are included in the CBC, DIFF, RET, and PLT-F measurement item groups.

In the blood cell analyzer 1, the CBC, DIFF, RET, and PLT-F measurement item groups are set as the basic item in order to measure any sample by at least one among the CBC, DIFF, RET, PLT-F measurement item groups. On the other hand, the single item HPC included in the HPC measurement item group is set as an additional item to be additionally measured according to the preference of the user.

[Blood Cell Analyzer 1 Measurement Operation]

The measurement operation of the blood cell analyzer 1 of the present embodiment is described below.

Figure 5:
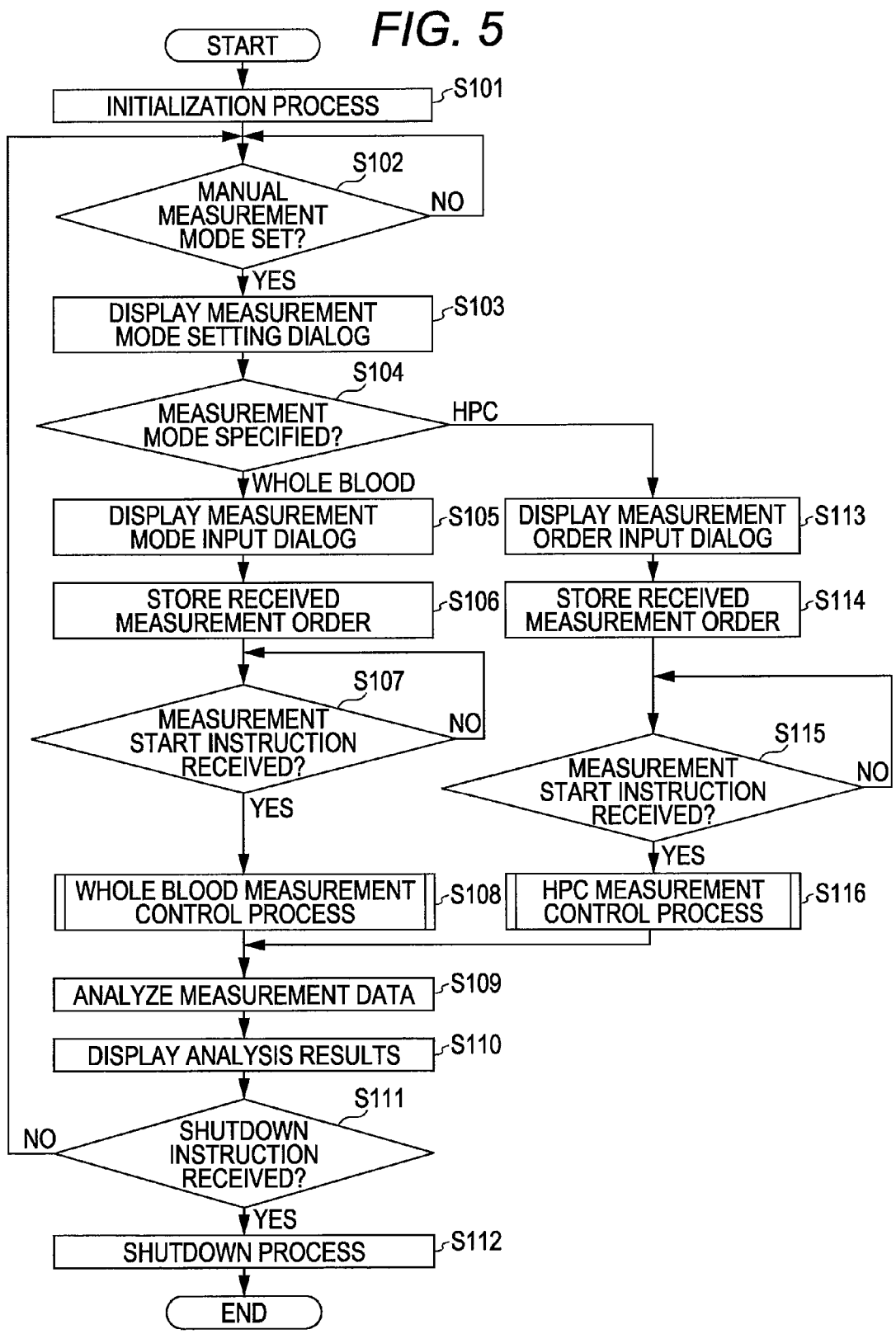
FIG. 5 is a flow chart showing the processing sequence of the information processing unit in the measurement operation of the blood cell analyzer of the embodiment.

FIG. 5 is a flow chart showing the processing sequence of the information processing unit 5 in the measurement operation of the manual measurement mode performed by the blood cell analyzer 1. When the blood cell analyzer 1 is turned ON, the CPU 51a of the information processing unit 5 executes an initialization process to initialize programs and values of various types of settings (step S101). The measurement unit 2 enters the measurement standby state (a state wherein measurement may start) by performing the initialization process.

In the measurement standby state, the user presses mode switch 26a to change from the sampler measurement mode to the manual measurement mode. At this time the sample container transporter 25 is fed from the front side of the measurement unit 2. An instruction setting the manual measurement mode is sent to the information processing unit 5 by pressing the mode switch 26a.

The CPU 51a of the information processing unit 5 determines whether an instruction setting the manual measurement mode are been received (step S102). When an instruction setting the manual measurement mode has not been received (S102: NO), the CPU 51a repeats the process of step S102.

Figure 6:
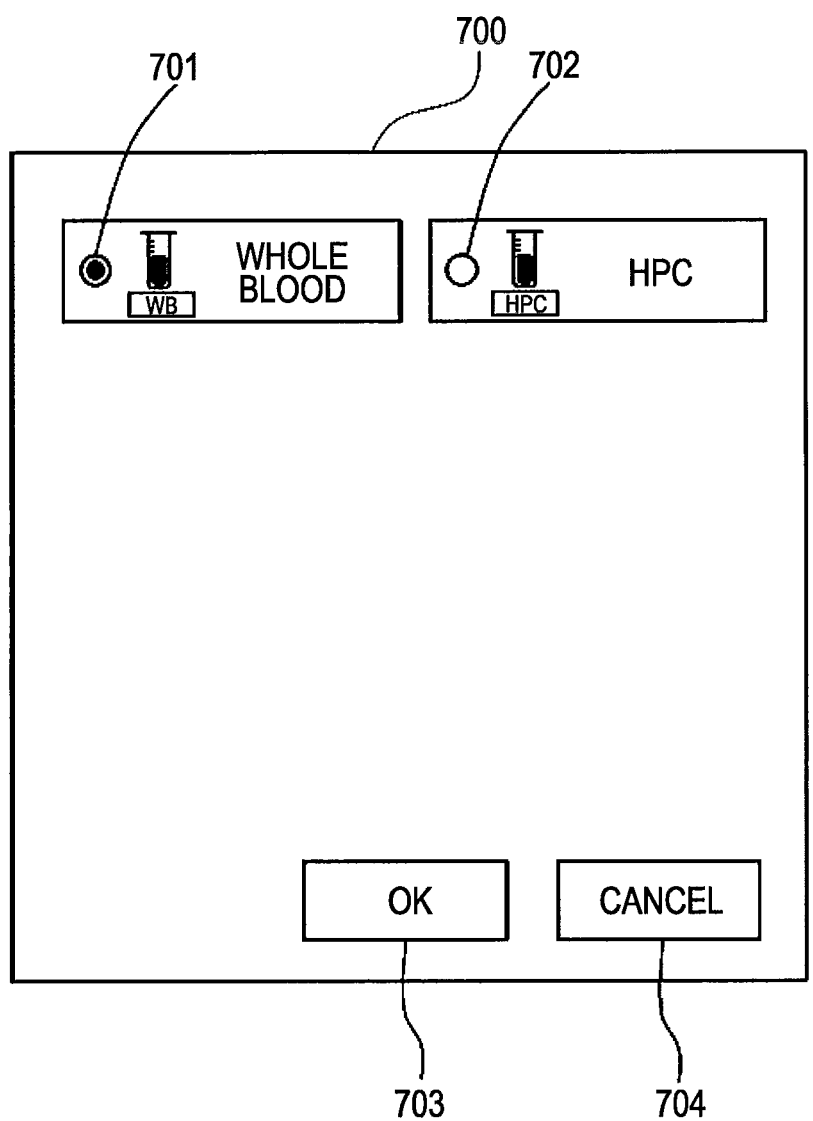
FIG. 6 shows the measurement mode setting dialog.

On the other hand, when an instruction setting the manual measurement mode has been received (S102: YES), the CPU 51a shows a measurement mode setting dialog on the display section 52 (step S103). FIG. 6 shows the measurement mode setting dialog. As shown in FIG. 6, the measurement mode dialog 700 has a radio button 701 for setting the whole blood measurement mode and a radio button 702 for setting the HPC measurement mode. The whole blood measurement mode measures basic items, and is a measurement mode for measuring blood cells such as red blood cells and white blood cells in whole blood. The HPC measurement mode is a measurement mode for detecting hematopoietic progenitor cells in addition to the measurement items in the whole blood measurement mode.

The user sets the measurement mode by selecting either the radio button 701 or 702. Note that the measurement mode default value is the whole blood measurement mode.

The measurement mode setting dialog 700 also has an OK button 703 and a cancel button 704. The user selects the OK button 703 when executing the measurement of a sample according to the set measurement mode after a measurement mode has been set by selecting the radio button 701 or 702. However, the user selects the cancel button 704 to stop a sample measurement.

The CPU 51a determines whether a measurement mode setting has been received (step S104). When a whole blood measurement mode setting is received (step S104: "whole blood"), the CPU 51a shows the measurement order dialog on the display section 52 (step S105).

Figure 7:
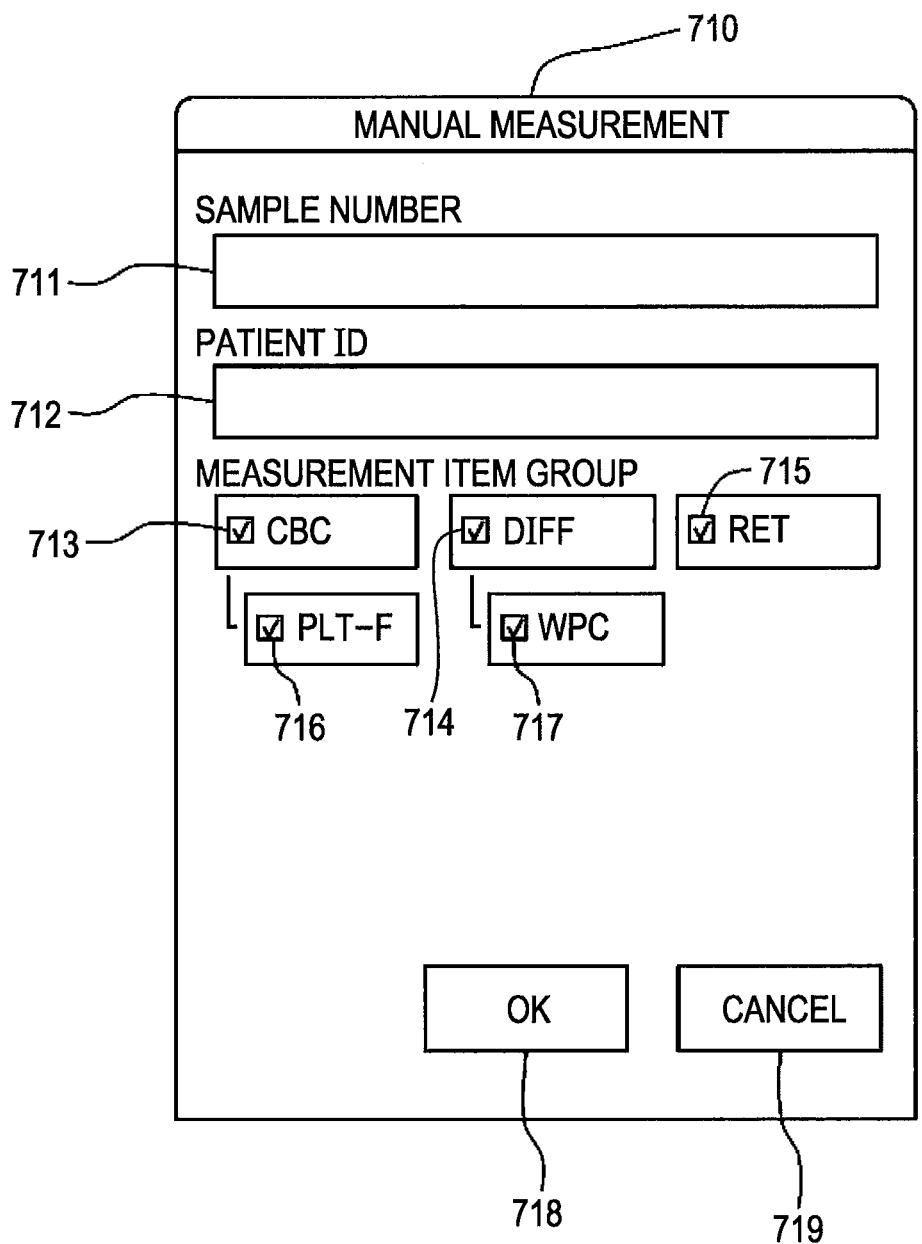
FIG. 7 shows the measurement order input dialog.

FIG. 7 shows the measurement order input dialog. The measurement order input dialog 710 has an input box 711 for entering the sample ID (sample number), and an input box 712 for entering the patient ID assigned to the patient from whom the blood sample was collected. The user enters the sample ID in the input box 711, and enters the patient ID in the input box 712 by operating the input section 53. The sample ID and the patient ID may also be input by reading the sample barcode adhered to the sample container T using a barcode reader connected to the information processing unit 5.

The measurement order input dialog 710 also has a plurality of check boxes 713 through 717 for specifying measurement items. The check boxes 713 through 717 are used to specify a measurement item group. Specifically, the check box 713 specifies CBC, check box 714 specifies DIFF, check box 715 specifies RET, check box 716 specifies PLT-F, and check box 717 specifies WPC. Note that CBC is a compulsory item in whole blood measurement, and the check box 713 is initially selected by default and cannot be rescinded.

The measurement order input dialog 710 also has an OK button 718 and a cancel button 719. The OK button 718 is selected when executing the measurement of a sample according to a measurement order in which a measurement item group has been specified by the user inputting the sample ID and the patient ID in the input boxes 711 and 712 and selecting at least one of the check boxes 713 through 717. However, the user selects the cancel button 719 to stop a sample measurement.

The user sends the measurement order to the information processing unit 5 by selecting the OK button 718 of the measurement order input dialog 710. The CPU 51a receives the measurement order and stores the measurement order on the hard drive 51d (step S106). After the measurement order is sent to the information processing unit 5, the user loads the sample container T in the sample container receiver 25b and presses the measurement start switch 26*b*. Thus, the measurement start instruction is received by the information processing unit 5, and the sample container T is moved into the measurement unit 2 together with the sample container transporter 25.

The CPU 51*a* determines whether a measurement start instruction has been received (step S107). When the measurement start instruction is not received (step S107: NO), the CPU 51*a* returns again to the process of step S107. On the other hand, when the measurement start instruction has been received step S107: YES), the CPU 51*a* executes the whole blood measurement control process (step S108) which is a control process to perform measurement of a sample in the whole blood mode (hereinafter referred to as "whole blood measurement") by the measurement unit 2. Details of the whole blood measurement control process are described later.

In the whole blood measurement control process, measurement are performed on the blood sample for the measurement items specified in the measurement order. The data (hereinafter referred to as "measurement data") generated by measuring the blood sample in the measurement unit tare transmitted to the information processing unit 5. The CPU 51*a* of the information processing unit 5 analyzes the received measurement data (step S109), and determines the measurement value (for example, blood cell count value) of each measurement item. The CPU 51*a* stores the obtained analysis results in the analysis result database 55, and shows the analysis results on the display section 52 (step S110).

Note that the sample container T from which the sample has been aspirated in the measurement operation is discharged from the measurement unit 2.

To stop the blood cell analyzer 1, the user transmits a shutdown instruction to the information processing unit 5 by operating the input section 53. The CPU 51*a* determines whether a shutdown instruction has been received (step S111), and returns to the process of step S102 when a shutdown instruction has not been received (step S111: NO). On the other hand, the CPU 51*a* executes the shutdown process (step S112) when a shutdown instruction has been received (step S111: YES), and the process ends.

When an HPC measurement mode setting is received (step S104: "HPC"), the CPU 51*a* shows the measurement order input dialog on the display section 52 (step S113). The measurement order input dialog with the HPC measurement mode set is a dialog that omits the plurality of check boxes 113 through 117 for issuing measurement item instructions from the measurement order input dialog 710 that is displayed when the whole blood measurement mode is set. That is, the measurement order input dialog with the HPC measurement mode set has an input box for entering the sample ID, and input box for entering the patient ID, check box for contacting the host, OK button, and cancel button.

In the HPC measurement mode, all measurement item groups other than WPC, that is, CBC, DIFF, RET, PLT-F, and HPC, are automatically selected. The user can input a measurement order specifying the measurement item group CBC, DIFF, RET, PLT-F, and HPC by inputting the sample ID and patient ID in the two input boxes. Then, the user selects the OK button in the measurement order input dialog to execute the measurements of the sample according to the measurement order after the measurement order has been entered. However, the user selects the cancel button to stop a sample measurement.

The CPU 51*a* receives the measurement order and stores the measurement order on the hard disk 51*d* when the user selects the OK button in the measurement order input dialog. After the measurement order is sent to the information processing unit 5, the user loads the sample container T in the sample container receiver 25*b* and presses the measurement start switch 26*b*. Thus, the measurement start instruction is received by the information processing unit 5, and the sample container T is moved into the measurement unit 2 together with the sample container transporter 25.

The CPU 51*a* determines whether a measurement start instruction has been received (step S115). When the measurement start instruction is not received (step S115: NO), the CPU 51*a* returns again to the process of step S115. On the other hand, when the measurement start instruction has been received step S115: YES), the CPU 51*a* executes the HPC measurement control process (step S116) which is a control process to perform measurement of a sample in the HPC measurement mode by the measurement unit 2. Details of the HPC measurement control process are described later.

In the HPC measurement control process, measurement of a blood sample is performed according to the measurement items included in each measurement item group excluding WPC. The measurement data generated by measuring the blood sample in the measurement unit 2 are transmitted to the information processing unit 5. The CPU 51*a* of the information processing unit 5 analyzes the received measurement data (step S109), stores the analysis results of the blood sample in the HPC measurement mode in the analysis result database 55, and shows the analysis results on the display section 52 (step S110). The subsequent processing is identical to the content of the previously described step S111 and the following steps.

<Whole Blood Measurement Control Process>

Figure 8:
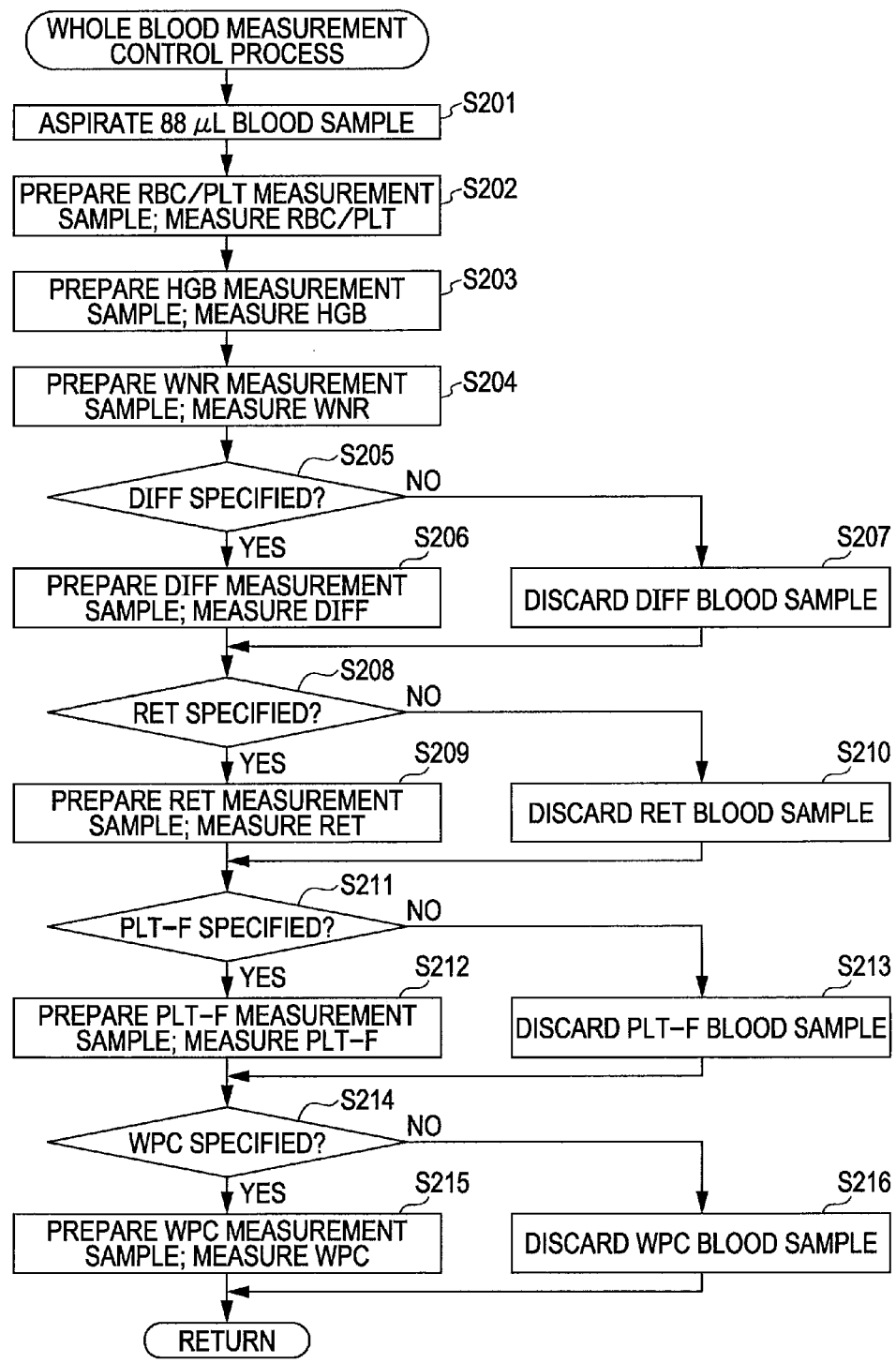
FIG. 8 is a flow chart showing the sequence of the whole blood measurement control process in the information processing unit of the blood cell analyzer of the embodiment.

The whole blood measurement control process is described below. FIG. 8 is a flow chart showing the sequence of the whole blood measurement control process performed in the information processing unit 5.

In the whole blood measurement control process, the CPU 51*a* first aspirates 88 μL of the blood sample in the measurement unit 2 (step S201). The 88 μL of the blood sample are used in the measurements of each measurement item of the whole blood measurement, and are not used for any other measurement. This process controls the measurement unit 2 to aspirate the 88 μL of the blood sample from the received sample container T by the sample aspirating unit 21.

The CPU 51*a* then prepares the RBC/PLT measurement sample, and measures RBC/PLT (step S202). This process prepares the RBC/PLT measurement sample by controlling the measurement unit 2 to discharge 4 μl of the blood sample from the aspirating tube 211 into the first mixing chamber 221, supplying 1 ml of diluting liquid from the diluting liquid container 201*a* into the first mixing chamber 221, and mixing the blood sample and diluting liquid within the first mixing chamber 221 by stirring. Part of the prepared RBC/PLT measurement sample is supplied to the first detection unit D1, and the RBC/PLT measurements are performed.

The CPU 51*a* then prepares the HGB measurement sample, and measures HGB (step S203). This process prepares the HGB measurement sample by controlling the measurement unit 2 to supply a predetermined amount of hemoglobin hemolytic agent from the hemoglobin hemolytic agent 201*b* into the first mixing chamber 221, and mixing the hemoglobin hemolytic agent and the remaining RBC/PLT measurement sample in the first mixing chamber 221 by stirring. The prepared HGB measurement sample is then supplied to the second detection unit D2, and the HGB measurement is performed.

The CPU 51*a* then prepares the WNR measurement sample, and the WNR measurement is performed (step S204). This process prepares the WNR measurement sample by controlling the measurement unit 2 to discharge 17 μl of the blood sample from the aspirating tube 211 into the third mixing chamber 223, supplying 1 ml of nucleated red blood cell detection hemolytic agent from the nucleated red blood cell detection hemolytic agent container 203a into the third mixing chamber 223, supplying 20 μL of nucleated red blood cell detection stain from the nucleated red blood cell detection stain container 203b into the third mixing chamber 223, and mixing the blood sample and reagents within the third mixing chamber 223 by stirring. The prepared WNR measurement sample is then supplied to the third detection unit D3, and the WNR measurement is performed.

The CPU 51a then determines whether DIFF is specified in the measurement order stored on the hard disk 51d (step S205). When DIFF is specified in the measurement order (step S205: YES), the CPU 51a causes the measurement unit 2 to prepare the DIFF measurement sample and perform the DIFF measurement (step S206), and the process then moves to step S208. This process prepares the DIFF measurement sample by controlling the measurement unit 2 to discharge 17 μl of the blood sample from the aspirating tube 211 into the second mixing chamber 222, supplying 1 ml of white blood cell classification hemolytic agent from the white blood cell classification hemolytic agent container 202a into the second mixing chamber 222, supplying 20 μL of white blood cell classification stain from the white blood cell classification stain container 202b into the second mixing chamber 222, and mixing the blood sample and reagents within the second mixing chamber 222 by stirring. The prepared DIFFR measurement sample is then supplied to the third detection unit D3, and the DIFF measurement is performed.

When DIFF is not specified in the measurement order (step S205: NO), the CPU 51a causes the measurement unit 2 to discard an amount of blood sample equal to the amount used to prepare the DIFF measurement sample (step S207), and the process then moves to step S208. Thus, 17 μL of blood sample is discharged from the aspirating tube 211.

The CPU 51a then determines whether RET is specified in the measurement order stored on the hard disk 51d (step S208). When RET is specified in the measurement order (step S208: YES), the CPU 51a causes the measurement unit 2 to prepare the RET measurement sample and perform the RET measurement (step S209), and the process then moves to step S211. This process prepares the RET measurement sample by controlling the measurement unit 2 to discharge 5 μl of the blood sample from the aspirating tube 211 into the fifth mixing chamber 225, supplying 1 ml of diluting liquid from the diluting liquid container 201a into the fifth mixing chamber 225, supplying 20 μL of reticulocyte detection stain from the reticulocyte detection stain container 205a into the fifth mixing chamber 225, and mixing the blood sample and reagent within the fifth mixing chamber 225 by stirring. The prepared RET measurement sample is then supplied to the third detection unit D3, and the RET measurement is performed. After the RET measurement sample has been supplied for the RET measurement, the liquid remaining in the fifth mixing chamber 225 is discarded and the fifth mixing chamber 225 is washed.

When RET is not specified in the measurement order (step S208: NO), the CPU 51a causes the measurement unit 2 to discard an amount of blood sample equal to the amount used to prepare the RET measurement sample (step S210), and the process then moves to step S211. Thus, 5 μL of blood sample is discharged from the aspirating tube 211.

The CPU 51a then determines whether PLT-F is specified in the measurement order stored on the hard disk 51d (step S211). When PLT-F is specified in the measurement order (step S211: YES), the CPU 51a causes the measurement unit 2 to prepare the PLT-F measurement sample and perform the PLT-F measurement (step S212), and the process then moves to step S214. This process prepares the PLT-F measurement sample by controlling the measurement unit 2 to discharge 5 μl of the blood sample from the aspirating tube 211 into the fifth mixing chamber 225, supplying 1 ml of diluting liquid from the diluting liquid container 201a into the fifth mixing chamber 225, supplying 20 μL of platelet detection stain from the reticulocyte detection stain container 205b into the fifth mixing chamber 225, and mixing the blood sample and reagent within the fifth mixing chamber 225 by stirring. The prepared PLT-F measurement sample is then supplied to the third detection unit D3, and the DIFF measurement is performed.

When PLT-F is not specified in the measurement order (step S211: NO), the CPU 51a causes the measurement unit 2 to discard an amount of blood sample equal to the amount used to prepare the PLT-F measurement sample (step S213), and the process then moves to step S214. Thus, 5 μL of blood sample is discharged from the aspirating tube 211.

The CPU 51a then determines whether WPC is specified in the measurement order stored on the hard disk 51d (step S214). When WPC is specified in the measurement order (step S214: YES), the CPU 51a causes the measurement unit 2 to prepare the WPC measurement sample and perform the WPC measurement (step S215). This process prepares the WPC measurement sample by controlling the measurement unit 2 to discharge 5 μl of the blood sample from the aspirating tube 211 into the fourth mixing chamber 224, supplying 1 ml of diluting liquid from the diluting liquid container 201a into the fourth mixing chamber 224, supplying 20 μL of immature cell detection stain from the immature cell detection stain container 204b into the fourth mixing chamber 224, and mixing the blood sample and reagent within the fourth mixing chamber 224 by stirring. The prepared WPC measurement sample is then supplied to the third detection unit D3, and the WPC measurement is performed. After the process of step S215 ends, the CPU 51a returns to the process at the call address of the whole blood measurement control process of the main routine.

On the other hand, when WPC is not specified in the measurement order (step S214: NO), the CPU 51a causes the measurement unit 2 to discard an amount of blood sample equal to the amount used to prepare the WPC measurement sample (step S216). Thus, 5 μL of blood sample is discharged from the aspirating tube 211. After the process of step S216 ends, the CPU 51a returns to the process at the call address of the whole blood measurement control process of the main routine.

In the whole blood measurement described above, the same amount (88 μL) of blood sample is normally aspirated regardless of which of the measurement items is specified, and blood samples at the same position in the aspirating tube 211 are normally used for identical measurement items. This is described in detail below.

Figure 9:
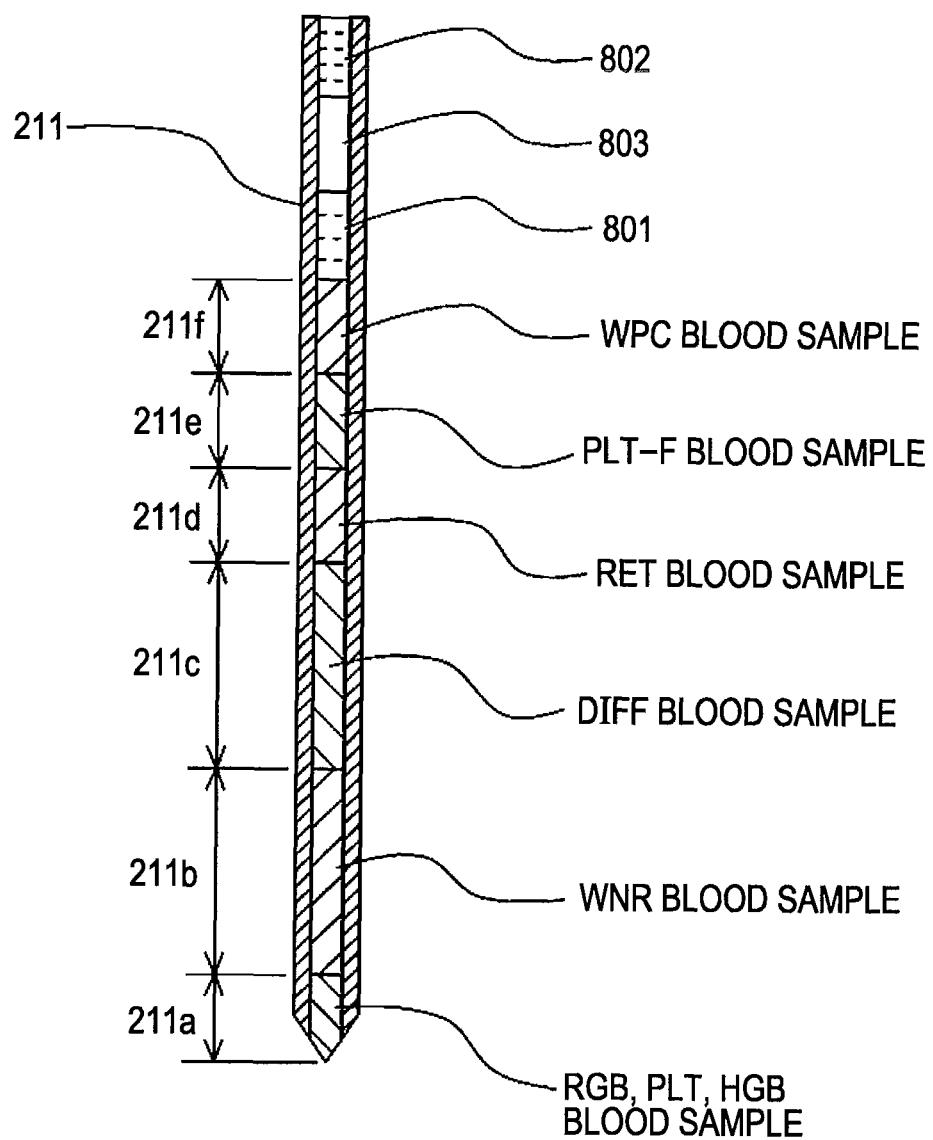
FIG. 9 is a cross sectional diagram schematically showing the condition of the aspirating tube when blood sample is aspirated.

FIG. 9 is a cross sectional schematic view showing the condition of the aspirating tube 211 when blood sample is aspirated. As shown in FIG. 9, 88 μL of blood sample 801 is aspirated into the aspirating tube 211 in the whole blood measurement. This can be realized by actuating the syringe pump 212 to move the diluting liquid 802 within the aspirating tube 211 when the aspirating tube 211 is loaded with diluting liquid 802 to the tip of the tube and inserted into the sample container T, then moving the blood sample within the sample container T into the aspirating tube. To inhibit dilution of the blood sample 802, an air layer 803 is present medially to the diluting liquid 802 and the blood sample 801.

The aspirated 88 µL of blood sample 801 is determined for the target measurement item by the position within the aspirating tube 211. That is, immediately after the 88 µL of blood sample is aspirated, that is, when the aspirated blood sample is not completely discharged, the blood sample at position 211a at the tip of the aspirating tube 211 is the blood sample used in RBC, PLT, and HGB measurement, and the blood sample at position 211b above the position 211a is used in the WNR measurement. The blood sample at position 211c above the position 211b is used in the DIF measurement, the blood sample at position 211d further above the position 211c is used in the RET measurement, the blood sample at position 211e above the position 211d is used in the PLT-F measurement, and blood sample at position 211f above the position 211e is used in the WPC measurement.

When measurement is only executed for specific measurement items in the whole blood measurement, the blood sample corresponding to measurement items that are not to be measured is discarded. That is, a blood sample corresponding to any measurement item that is not a measurement object is not used for the measurement of another measurement item, and the blood sample at the position corresponding to this measurement item is only used to measure this particular measurement item. For example, when only performing CBC and RET measurements, the blood samples at position 211a is used for RBC, PLT, and HGB measurements, whereas the blood sample at position 211b is used for the WNR measurement When the DIFF measurement is not performed, the blood sample at position 211c is discarded, and the blood sample at position 211d is used for RET measurement. Since PLT-F and WPC measurements are not performed, the blood samples at positions 211e and 211f are discarded.

When diluting liquid is moved via the operation of the syringe pump 212 in the aspiration of the blood sample, a small amount of the diluting liquid adheres to the inner wall of the tube path through which the diluting liquid passes. The blood sample is mixed with the diluting liquid in this area when the blood sample rises from the sample container T Since the mixing of the blood sample and the diluting liquid occurs near the air layer 803, the blood sample at the positions near the air layer 803 has a reduced concentration, and the blood sample at positions separated from the air layer 803 has a higher concentration. Since the blood sample within the aspirating tube 211 has different concentration depending on the position of the sample within the tube, when measuring a single measurement item using blood sample at the position of the tip of the aspirating tube one time and using blood sample at a position near the air layer 803 in the aspirating tube 211 another time, the degree of dilution of the blood samples used in the measurements will mutually differ so that accurate measurement results cannot be obtained. Therefore, measurement of identical measurement items performed even on different blood samples under common aspiration conditions can be performed while suppressing any influence on the measurement results due to different degrees of dilution between the blood samples by determining the position within the aspirating tube 211 of the blood sample to be used in each measurement item.

<HPC Measurement Control Process>

Figure 10:
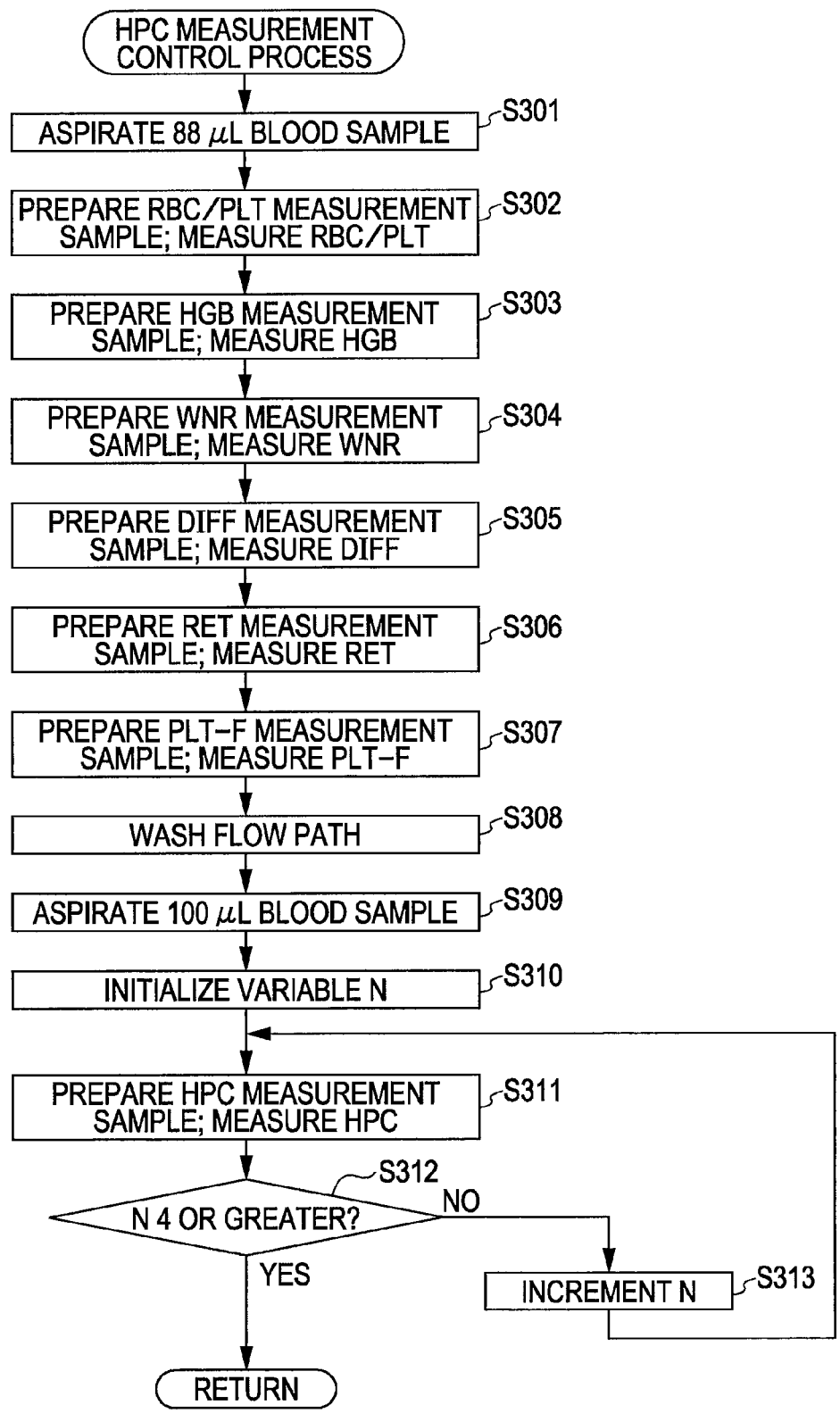
FIG. 10 is a flow chart showing the sequence of the HPC measurement control process in the information processing unit of the blood cell analyzer of the embodiment.

The HPC measurement control process is described below. FIG. 10 is a flow chart showing the sequence of the HPC measurement control process performed in the information processing unit 5.

In the HPC measurement mode, preparation of the HPC measurement sample and the measurement of the HPC measurement sample (hereinafter referred to as "HPC measurement") are performed several times (for example, four times) after executing a whole blood measurement in which all measurement item group except WPC are specified. In the HPC measurement control process, the CPU 51a first aspirates 88 µL of the blood sample in the measurement unit 2 (step S301). The 88 µL of the blood sample is used in the measurements of each measurement item of the whole blood measurement, and is not used for the HPC measurement. This process controls the measurement unit 2 to aspirate the 88 µL of the blood sample from the received sample container T by the sample aspirating unit 21.

The CPU 51a then prepares the RBC/PLT measurement sample, and measures RBC/PLT (step S302). The CPU 51a then sequentially executed in the measurement unit 2 HGB measurement sample preparation and HGB measurement (step S303), WNR measurement sample preparation and WNR measurement (S304), DIFF measurement sample preparation and DIFF measurement (S305), RET measurement preparation and RET measurement (S306), and PLT-F measurement sample preparation and PLT-F measurement (S307). Note that the process of step S302 is identical to the process of step S202 the process of step S303 is identical to the process of step S203, the process of step S304 is identical to the process of step S204, the process of step S305 is identical to the process of step S206, the process of step S306 is identical to the process of step S209, and the process of step S307 is identical to the process of step S212.

The CPU 51a then discards the remaining measurement sample in the aspirating tube 211 in the measurement unit 2, and executes a washing operation of the flow path of the measurement sample including the aspirating tube 211 (step S308). Thus, the 88 µL of measurement sample aspirated one time is completed discharged from the aspirating tube 211.

The CPU 51a then causes the measurement unit 2 to aspirate 100 µL of measurement sample (step S309). The 100 µL of measurement sample is used for the HPC measurement, and is not used to measure any other measurement item. This process controls the measurement unit 2 to aspirate the 100 µL of the blood sample from the received sample container T by the sample aspirating section 21.

The CPU 51a then stores [0] mas the initial value of the variable N representing the number of times of HPC measurement in the RAM 51c (step S310), and causes the measurement unit 2 to perform HPC measurement sample preparation and HPC measurement (step S311). This process prepares the HPC measurement sample by controlling the measurement unit 2 to discharge 17 µl of the blood sample from the aspirating tube 211 into the fourth mixing chamber 224, supplying diluting liquid from the diluting liquid container 201a into the fourth mixing chamber 224, supplying immature cell detection stain from the immature cell detection stain container 204b into the fourth mixing chamber 224, and mixing the blood sample and reagent within the fourth mixing chamber 224 by stirring. The prepared HPC measurement sample is then supplied to the third detection unit D3, and the HPC measurement is performed.

The CPU 51a determines whether the value of the variable N is [4] or greater (step S312); when the value is less than [4] (step S312: NO), the value of the variable N is incremented by [1] (step S313) and the process moves to step S311. Thus, HPC measurement sample preparation and HPC are performed again.

When the value of the variable N is [4] or greater in step S312 (step S312: YES), the CPU 51a returns to the process of the call address of the HPC measurement control process of the main routine.

In the HPC measurement mode, the HPC measurement is performed four times as mentioned above. That is, the measurement data of four HPC measurements are included in the measurement data transmitted from the measurement unit 2 to the information processing unit 5. a process is performed to average the measurement values of the four obtained data in the process of step S109 when measurement samples are measured in the HPC measurement mode.

In the blood sample measurement in the HPC measurement mode, 88 µL of blood sample is first aspirated and measurements performed of basic measurement items (measurement items that are measurable in the whole blood measurement mode) using the 88 µL of blood sample. Thereafter, 100 µL of blood sample is aspirated and the HPC measurement is performed using the 100 µL of blood sample. Thus, the measurement of basic measurement items (CBC, DIFF, RET, PLT-F) can be performed under the same blood sample aspiration conditions as in the whole blood mode, and effects of variation in the measurement sample concentration due to different aspiration conditions can be suppressed.

The same amount (88 µL) of blood sample is aspirated and measured even when the measurement items of the measurement in the whole blood measurement mode is different from the measurement items of the measurement in the basic item measurement of the HPC measurement mode. When performing the measurement of the basic items, therefore, the degree of dilution of the blood sample is normally identical and the effect of variations in the concentration of the blood samples is suppressed because the amount of aspirated blood sample is normally the same regardless of whether the measurement mode is the HPC measurement mode or the whole blood measurement mode, and regardless of the measurement item to be measured.

Figure 11:
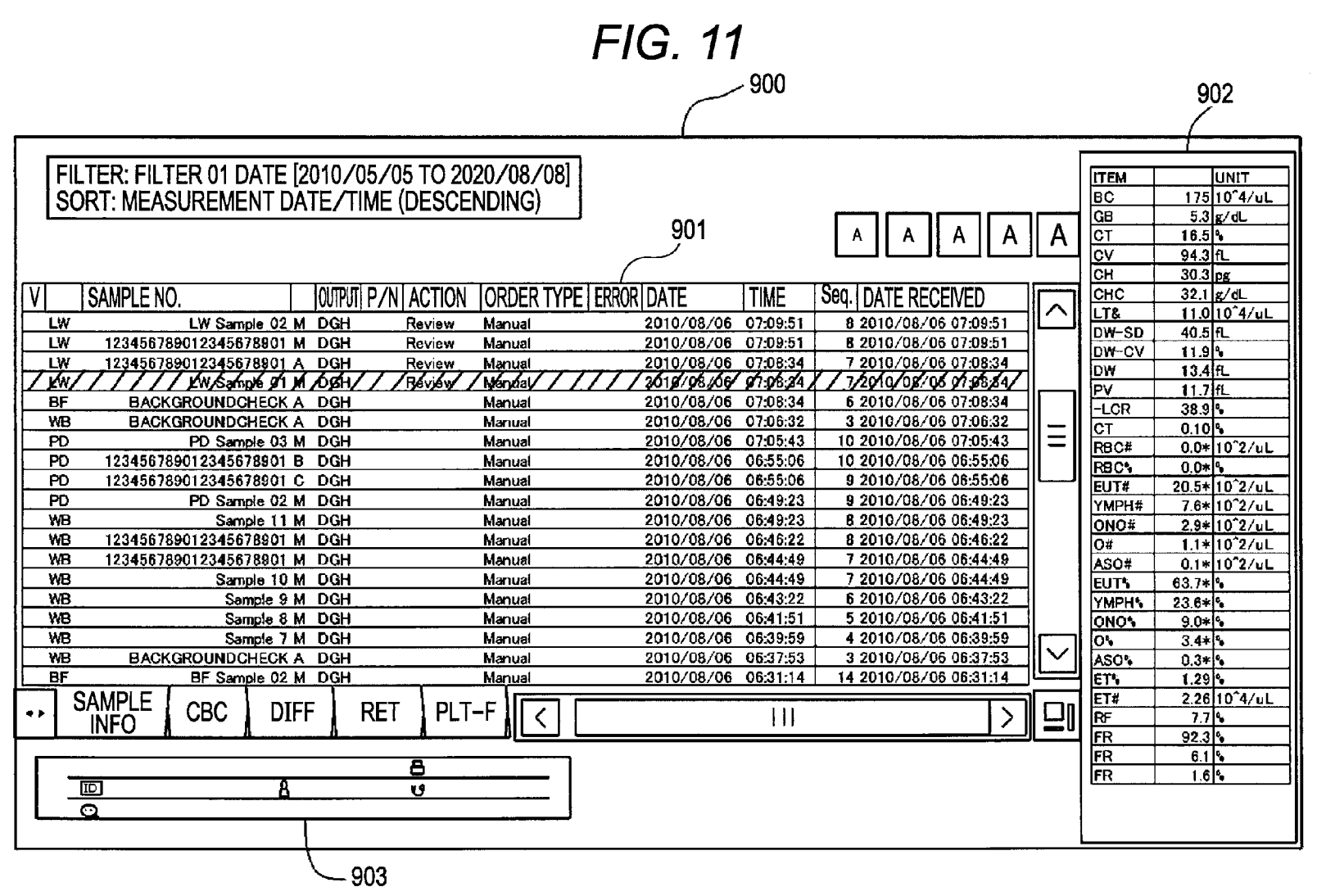

The screen showing the analysis results obtained through the measurement operation is described below. FIGS. 11 and 12 show examples of the analysis result list screen of the blood cell analyzer 1. The analysis result list screen is shown on the display section 52 when the user performs a predetermined operation through the input section 53, that is, an operation that issues an instruction to display the analysis result list screen. As shown in FIGS. 11 and 12, the analysis result list screen 900 has a list display area 901 for displaying a list of analysis result data stored in the analysis result database 55. The list display area 901 shows a plurality of analysis result data extracted from the analysis result database 55 in a list format. The list display area 901 includes a region for displaying the sample number (sample ID), region for displaying the day of the measurement, and region for showing the time of the measurement; the user can search for analysis data corresponding to a blood sample for which he wants to verify the measurement information by referring to the analysis result data shown in list format in the list display area 901. Optional lines in the list display area 901 are selectable by mouse click operation or the like to select analysis result data corresponding to the selected line. When the user selects a single line, the background color of the selected line is switched from a color (for example, white) indicating the line is not selected to a color (for example, blue) indicating the line is selected. In FIGS. 11 and 12, the hatched lines on a line indicate the line is selected.

The analysis result list screen 900 also has a measurement value display area 902 for showing a list of measurement values on the right of the list display area 901, and a patient attribute information display area 903 for showing patient attribute information below the list display area 901. When analysis result data are selected in the list display area 901, the measurement values included in the analysis result data are shown in the measurement value display area 902, and the patient attribute information contained in the analysis result data is shown in the patient attribute information display area 903.

FIG. 11 shows the analysis result list screen 900 when blood sample analysis data measured in the whole blood measurement mode are selected. Measurement values for the measured basic items are shown in the measurement value display area 902 in FIG. 11.

FIG. 12 shows the analysis result list screen 900 when blood sample analysis data measured in the HIPC measurement mode are selected. The analysis results for blood sample measured in the HIPC measurement mode include measurement results for the HPC measurement described above. As shown in FIG. 12, when the analysis results of the blood sample measured in the HPC measurement mode are selected, the measurement value display area 902 shows the HPC measurement values 904 below the measurement values of the basic items.

Figure 13:
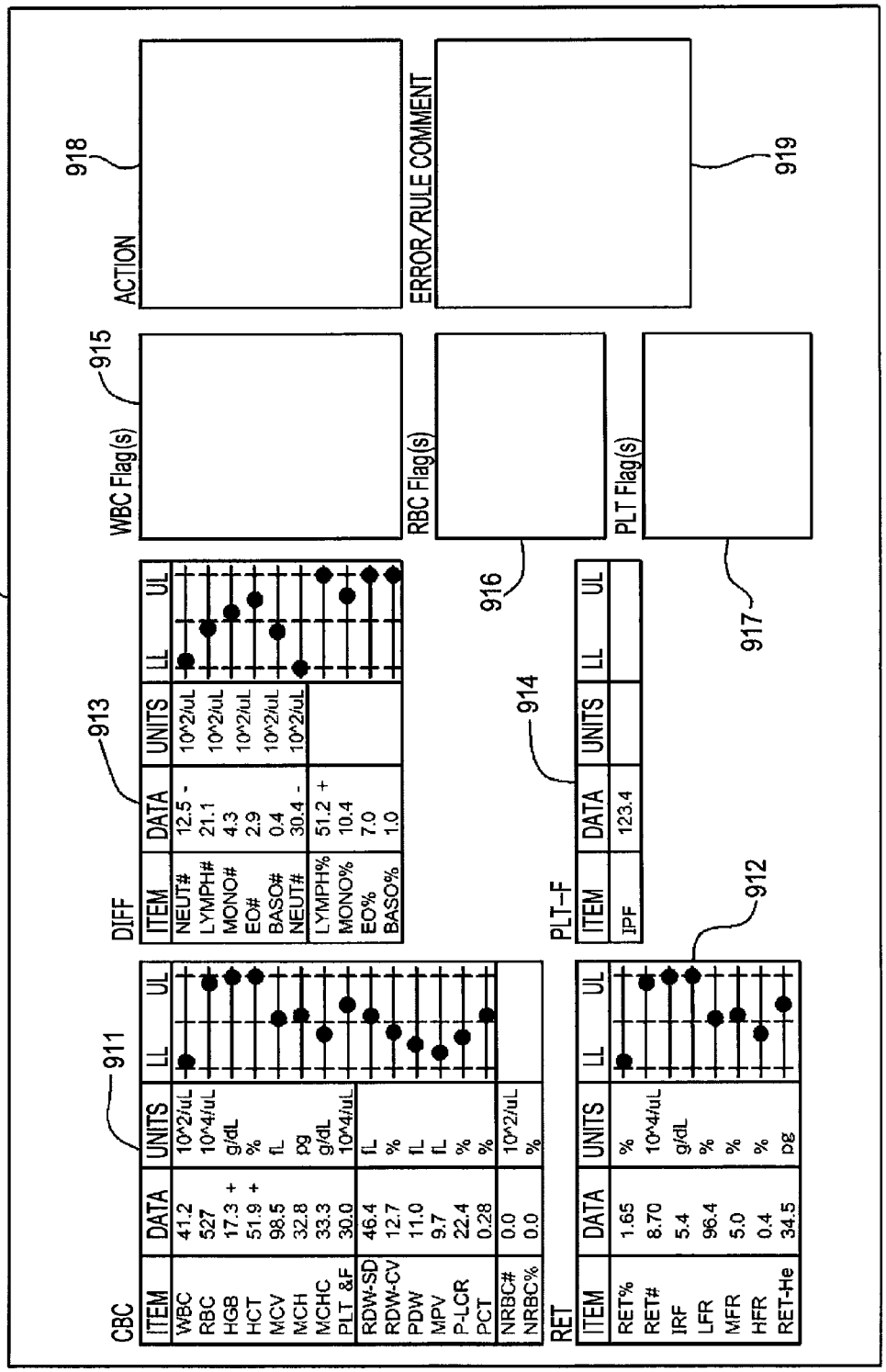
FIG. 13 shows an example of the analysis result details screen of the blood cell analyzer of the embodiment.
Figure 14:
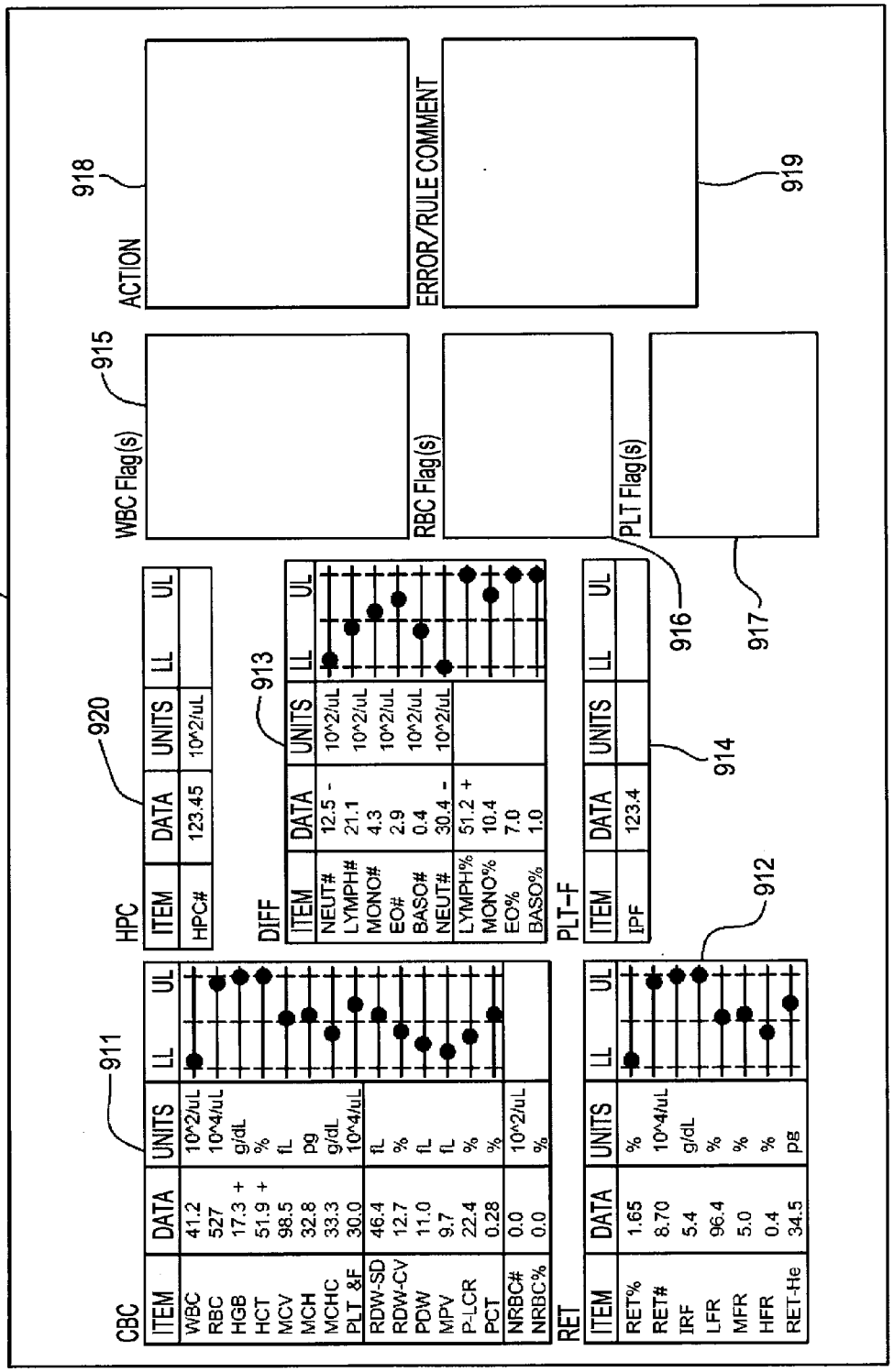
FIG. 14 shows another example of the analysis result details screen of the blood cell analyzer of the embodiment.

FIGS. 13 and 14 show examples of the analysis result detail screen. The analysis result detail screen is a screen shown on the display section 52 in step S110 as described above. Analysis result data appear in the analysis result detail screen shown on the display section 52 when the user performs an operation to issue an instruction to display the analysis result detail screen using analysis result data by, for example, double clicking one line in the list display area 901 of the analysis result list screen 900.

FIG. 13 shows the analysis result detail screen displaying the analysis result data of a blood sample measured in the whole blood measurement mode. The analysis result detail screen 910 has a plurality of regions for displaying measurement values of each measurement item group, that is, a CBC measurement value display area 911, RET measurement value display area 912, DIFF measurement value display area 913, and PLT-F measurement value display area 914. The CBC measurement value display area 911 shows the measurement values for items related to CBC, including WBC, RBC, HGB, and PLT. The RET measurement value display area 912 shows the measurement values for items related to RET, including RET % (ratio of the number of reticulocytes to the sum of the number of mature red blood cells and number of reticulocytes), RET# (reticulocyte count) and the like. The DIFF measurement value display area 913 shows measurement values for measurement items related to DIFF, including NEUT# (neutrophil count), LYMPH#*lymphocyte count), EO# (eosinophil count), MONO# (monocyte count). The PLT-F measurement value display area 914 shows the measurement values of IPF (ratio of immature platelets), which is a measurement item related to PLT-F. Specific measurement items are also shown in a graph indicating the position of the measurement value in the normal range in the CBC measurement value display area 911, RET measurement value display area 912, DIFF measurement value display area 913, and PLT-F measurement value display area 914.

The analysis result detail screen 910 shows only information corresponding to the measurement item groups that include measurement values in the analysis result data in the CBC measurement value display area 911, RET measurement value display area 912, DIFF measurement value display area 913, and PLT-F measurement value display area 914 That is, only CBC measurement values are included in the analysis result data; when DIFF, RET, and PLT-F measurement values are not included (that is, when only CBC is specified in the measurement order received when measuring a blood sample), the CBC measurement display area 911 is shown in the analysis result detail screen, and the RET measurement value display area 912, DIFF measurement value display area 913, and PLT-F measurement value display area 914 are not shown.

The analysis result detail screen 910 also has a WBC flag display area 915 to show blood sample measurement results and information indicating an abnormality when an abnormality related to WBC is detected, RBC flag display area 916 to show information indicating an abnormality when an abnormality related to RBC is detected, and a PLT flag display area 917 to show information indicating an abnormality when an abnormality related to PLT is detected, an action display area 918 to show information indicating a measurement result must be verified, and an error/rule comment display area 919 to show information indicating the occurrence of a measurement error or re-measurement is required.

FIG. 14 shows the analysis result detail screen displaying the analysis result data of a blood sample measured in the HPC measurement mode. The analysis result detail screen 910 shown in FIG. 14 has an HPC measurement value display area 920 in addition to the CBC measurement value display area 911, RET measurement value display area 912, DIFF measurement value display area 913, and PLT-F measurement value display area 914. The HPC measurement value display area 920 shows the measurement values of HPC# (number of hematopoietic progenitor cells), which is a measurement item related to HPC.

According to this structure described above, when the blood cell analyzer 1 measures samples in the whole blood measurement mode a fixed amount (88 µL) of the blood sample is aspirated from the sample container T in a single aspiration operation regardless of the measurement item, and the measurement of the blood sample is rapidly performed. When the blood cell analyzer 1 measures samples in the HPC measurement mode, that is, when the basic items (CBC, RET, DIFF, PLT-F) and HPC items are to be measured, the same amount (88 µL) of blood sample as in the whole blood measurement mode is aspirated from the sample container in a single aspiration operation separately from the aspiration of blood sample for measuring HPC items, and the basic items (CBC, DIFF, RET, PLT-F) are measured using this blood sample to suppress an influence on the measurement result of the basic items that might occur due to variation in the amount of aspirated blood sample. Note that although the amount of sample required in the HPC measurement mode (88 µL for the basic items+100 µL for the HPC items) is aspirated even in the whole blood measurement mode in order to prevent variation in the amount of aspirated blood sample, only the blood sample to be used for the basic items is aspirated in the whole blood measurement mode of the present embodiment. Thus, sample to be used for HPC items is not aspirated insofar as measurement of HPC items is not required. Note that even if measurement items are later added to the blood cell analyzer 1 in a version upgrade of the measurement program, the measurement results of the basic items remain unaffected and the additional measurement items can be measured by separately aspirating sample for the basic items and aspirating sample for the additional items.

There is a possibility of a measurement error occurring when measuring a component that is scarce in peripheral blood such as hematopoietic progenitor cells, since a single measurement may show no target component content detected in a prepared measurement sample. In the blood cell analyzer of the present embodiment, an HPC measurement sample is prepared four times from a single blood sample in the HPC measurement mode, and the HPC measurement is performed four times. Therefore, even when the component (hematopoietic progenitor cells) to be measured is not in sufficient quantity to be detectable in a single HPC measurement sample, this component may be in sufficient quantity to be detectable in another HPC measurement sample, so that the component can be detected with high reliability by performing measurements four times. Note that the number of HPC measurement sample preparations and HPC measurements is not limited to four and may be another plural number of times.

Other Embodiments

Although the above embodiment has been described in terms of the blood cell analyzer 1 that receives a measurement order in which the user has specified a measurement item group and performs measurement of the blood sample according to the measurement order, the present invention is not limited to this arrangement. A measurement order that directly specifies each measurement item (RBC, PLT, HGB, WBC, HPC) associated with a measurement item group may be received, and the measurement of the blood sample can be performed according to this measurement order. In this case, for example, when a measurement order specifying RBC, PLT, WBC, and RET is received, a first amount of blood sample is aspirated and measurements are performed for RBC, PLT, WBC, and RET using this aspirated blood sample; when a measurement order specifying RBC, PLT, WBC, and HPC is received, the first amount of blood sample is aspirated and RBC, PLT, and WBC measurements are performed using this aspirated blood sample, then a second amount of blood sample is aspirated and RET measurement is performed using this aspirated blood sample.

Although the above embodiment is described only in terms of operation in the manual measurement mode, the present invention also is realized in the sampler measurement mode.

Although the measurement unit and the information processing unit are provided separately in the above embodiment, the present invention is not limited to this configuration. A blood cell analyzer also may provide functions corresponding to the measurement unit and functions corresponding to the information processing unit within a single housing.

Although the measurement unit 2 is not provided with a calculation unit such as a CPU and the CPU 51*a* of the information processing unit 5 performs operational control of the measurement unit 2 in the above embodiment, the present invention is not limited to this configuration. The measurement unit also may be provided with a controller configured by a CPU and memory so that operational control of the measurement unit is performed by this controller.

Although a single computer 5*a* performs all processing of the computer program 54*a* in the above embodiment, the present invention is not limited to this configuration inasmuch as processes identical to those of the computer program 54*a* also may be distributed and executed by a plurality of devices (computers) as a distributed system.

The above embodiment has been described by way of examples of an operation to aspirate a blood sample to be used for basic items and supply the aspirated blood sample to a sample preparation section, and an operation to aspirate blood sample to be used for measurement of hematopoietic progenitor cells and supply the aspirated blood sample to a sample preparation section when measurement of hematopoietic progenitor cells is performed in addition to measurement of basic items (CBC, DIFF and the like), however, the present invention is not limited to these examples. For example, when measurement of a malaria parasite or CRP (C-reactive protein) is enabled in addition to measurement of basic items through a version upgrade of the computer program 54a, an operation may be performed to aspirate blood sample to be used for basic items and supply the aspirated blood sample to a sample preparation section, and an operation may be performed to aspirate blood sample to be used for malaria parasite or CRP measurement and supply the aspirated blood sample to a sample preparation section. Thus, the additional measurement of malaria parasite or CRP can be performed without reducing the measurement accuracy of basic items.

Although NRBC (nucleated red blood cells) is included in the CBC measurement item group in the above embodiment, the present invention is not limited to this arrangement. NRBC may be excluded from CBC and a check box for selecting NRBC may be provided separately from the check box for selecting CBC in the measurement order input dialog 710.

What is claimed is:

1. A blood cell analyzer, comprising:
a sample aspirating section which comprises an aspiration tube for aspirating a blood sample, and which aspirates a blood sample from a sample container by using the aspiration tube;
a sample preparing section configured to prepare a measurement sample from the blood sample aspirated by the sample aspirating section and a reagent;
a measuring section configured to measure the measurement sample prepared by the sample preparing section; and
an information processing unit comprising a processor and a memory that stores a program to be executed by the processor to:
control the sample aspirating section so as to perform a first sample supplying operation in response to receiving a first measurement order to only measure a complete blood count measurement item and one or more measurement items included in a first group with respect to the blood sample, wherein the first sample supplying operation includes aspirating the blood sample by a first amount and supplying the aspirated blood sample to the sample preparing section; and
control the sample aspirating section so as to perform a second sample supplying operation and a third sample supplying operation in response to receiving a second measurement order to measure a complete blood count measurement item and one or more measurement items included in a second group different from the first group with respect to the blood sample, wherein the second sample supplying operation includes aspirating the blood sample by the first amount for the complete blood count measurement item and supplying the aspirated blood sample to the sample preparing section, and the third sample supplying operation includes aspirating the blood sample by a second amount for one or more measurement items included in the second group and supplying the aspirated blood sample to the sample preparing section,
wherein the complete blood count measurement item comprises measuring the amount of red blood cells, platelets, hemoglobin, and white blood cells in the aspirated blood sample,
wherein the first group comprises at least one of a white blood cell classification item for classifying white blood cells into a plurality of groups, a measurement item related to reticulocytes, a measurement item related to nucleated red blood cells, a measurement item related to immature blood cells, and a measurement item related to abnormal lymphocytes; and
wherein the second group comprises at least one of a measurement item relating to hematopoietic progenitor cells, and a measurement item relating to malaria parasite.

2. The blood cell analyzer of claim 1, wherein
the sample preparing section is configured to prepare the measurement sample by diluting the blood sample with a diluting liquid; and
the sample aspirating section is configured to aspirate the blood sample from the sample container when a diluting liquid has been loaded in the aspirating tube and an air layer has been formed at a tip end of the aspirating tube.

3. The blood cell analyzer of claim 1, wherein
the first amount is an amount of blood sample required for the complete blood count measurement item and all measurement items included in the first group.

4. The blood cell analyzer of claim 1, wherein
the second amount is greater than the first amount.

5. The blood cell analyzer of claim 1, wherein
the second sample supplying operation is performed before the third sample supplying operation.

6. The blood cell analyzer of claim 1, wherein
the program of the memory of the information processing unit is used to measure a blood sample, and
the one or more measurement items included in the second group are measurement items added through a version upgrade of the measurement program stored in the memory.

7. The blood cell analyzer of claim 1, wherein
when the information processing unit has received the first measurement order to measure a first measurement item and a second measurement item included in the first group with respect to the blood sample, the information processing unit controls the sample aspirating section to supply, from the blood sample of the first amount aspirated in the aspirating tube, the blood sample in a first region on the tip end side of the aspirating tube to the sample preparing section for the first measurement item, and to supply the blood sample in a second region at the base end side of the aspirating tube to the sample preparing unit for the second measurement item; and
even when the information processing unit has not received an order to measure the first measurement item but has received an order to measure the second measurement item, the information processing unit controls the sample aspirating section to supply, from the blood sample of the first amount aspirated in the aspirating tube, the blood sample in the second region to the sample preparing section to be used for measuring the second measurement item.

8. The blood cell analyzer of claim 7, wherein
the sample preparing section comprises a first chamber for preparing a measurement sample to be used for the first measurement item, and a second chamber for preparing a measurement sample to be used for the second measurement item; and
the sample aspirating section supplies the blood sample in the first region of the aspirating tube to the first chamber, and supplies the blood sample in the second region of the aspirating tube to the second chamber.

9. The blood cell analyzer of claim 1, wherein
when the information processing unit has received the second measurement order to measure the one or more measurement items of the second group with respect to the blood sample, the information processing unit is configured to control the sample aspirating section to allocate the aspirated second amount of blood sample into a plurality of aliquots, control the sample preparing section to prepare a plurality of measurement samples from the aliquots of blood sample allocated by the sample aspirating section and reagent, control the measurement section to measure the plurality of measurement samples prepared by the sample preparing section, and generate measurement results of the one or more measurement items of the second group based on the measurement data of the plurality of measurement samples obtained by the measurement section.

10. The blood cell analyzer of claim 9, wherein
the sample preparing section comprises a chamber for preparing a measurement sample to be used for the one or more measurement items of the second group; and
the information processing unit supplies a part of the aspirated second amount of blood sample to the chamber and prepares a first measurement sample in the chamber, and after measurement of the first measurement sample, supplies another part of the second amount of blood sample to the chamber and prepares a second measurement sample in the chamber, then measures the second measurement sample.

11. The blood cell analyzer of claim 1, further comprising a display,
wherein the information processing unit controls the display to show measurement results of the measurement items of the first group and the second group on a same screen when the information processing unit has received the first measurement order and the second measurement order to measure the measurement items of the first group and the second group with respect to the blood sample.

12. The blood cell analyzer of claim 1, wherein
the information processing unit receives a selection of one of a first measurement mode and a second measurement mode,
when the first measurement mode has been selected, the information processing unit receives the first measurement order only for one or more measurement items selected by a user from the first group, and
when the second measurement mode has been selected, the information processing unit automatically receives the second measurement order for a predetermined measurement item included in the first group and the second group.

13. The blood cell analyzer of claim 12, further comprising an input section and a display,
wherein the information processing unit shows a selection screen having a plurality of measurement items included in the first group when the first measurement mode has been selected, and receives the first measurement order for one or more measurement items selected from the selection screen through the input section.

14. The blood cell analyzer of claim 1, wherein
the sample aspirating section comprises a pump to move the blood sample in the sample container from a tip end of the aspirating tube into the aspirating tube; and
wherein the pump discharges the blood sample contained in the aspirating tube from the tip end of the aspirating tube to the sample preparing section.

15. A blood cell analyzing method, comprising:
a step of receiving an order of a measurement item with respect to a blood sample;
a step of aspirating the blood sample in a sample container using an aspirating tube, and supplying the aspirated blood sample to a sample preparing section to prepare a measurement sample to be used in a measurement;
a step of preparing the measurement sample from a reagent and the blood sample supplied to the sample preparing section; and
a step of measuring the prepared measurement sample, wherein
when a first measurement order has been received to only measure a complete blood count measurement item and one or more measurement items included in a first group in the receiving step, a first sample supplying operation is performed in the supplying step, wherein the first sample supplying operation comprises an operation of aspirating the blood sample by a first amount and an operation of supplying the aspirated blood sample to the sample preparing section; and
when a second measurement order has been received to measure a complete blood count measurement item and one or more measurement items included in a second group different from the first group in the receiving step, a second sample supplying operation and a third sample supplying operation are performed in the supplying step, wherein the second sample supplying operation comprises an operation of aspirating the blood sample by the first amount for the complete blood count and an operation of supplying the aspirated blood sample to the sample preparing section, and the third sample supplying operation comprises an operation of aspirating the blood sample by a second amount for the one or more measurement items of the second group and an operation of supplying the aspirated blood sample to the sample preparing section,
wherein the complete blood count measurement item comprises measuring the amount of red blood cells, platelets, hemoglobin, and white blood cells in the aspirated blood sample,
wherein the first group comprises at least one of a white blood cell classification item for classifying white blood cells into a plurality of groups, a measurement item related to reticulocytes, a measurement item related to nucleated red blood cells, a measurement item related to immature blood cells, and a measurement item related to abnormal lymphocytes; and
wherein the second group comprises at least one of a measurement item relating to hematopoietic progenitor cells, and a measurement item relating to malaria parasite.

16. The blood cell analyzing method of claim 15, wherein
in the supplying step, the blood sample is aspirated from the sample container when a diluting liquid has been loaded in the aspirating tube and an air layer has been formed at a tip end of the aspirating tube; and
in the preparing step, a measurement sample is prepared by diluting the blood sample with a diluting liquid.

17. At least one non-transitory storage medium which stores programs executable collectively by at least one processor to perform processes comprising:
receiving an order of a measurement item with respect to a blood sample; and
controlling a sample aspirating section to aspirate a blood sample in a sample container using an aspirating tube, and supplying the aspirated blood sample to a sample preparing section, wherein
the processor controls the sample aspirating section so as to perform a first sample supplying operation when a first measurement order has been received to only measure a complete blood count measurement item and one or more measurement items included in a first group with respect to the blood sample, wherein the first sample supplying operation comprises an operation of aspirating the blood sample by a first amount and an operation of supplying the aspirated blood sample to the sample preparing section; and the processor controls the sample aspirating section so as to perform a second sample supplying operation and a third sample supplying operation when a second measurement order instruction has been received to measure a complete blood count measurement item and one or more measurement items included in a second group different from the first group with respect to the blood sample, wherein the second sample supplying operation comprises an operation of aspirating the blood sample by the first amount for the complete blood count measurement item and an operation of supplying the aspirated sample to the sample preparing section, and the third sample supplying operation comprises an operation of aspirating the blood sample by a second amount for the one or more measurement items of the second group and an operation of supplying the aspirated sample to the sample preparing section, wherein the complete blood count measurement item comprises measuring the amount of red blood cells, platelets, hemoglobin, and white blood cells in the aspirated blood sample, wherein the first group comprises at least one of a white blood cell classification item for classifying white blood cells into a plurality of groups, a measurement item related to reticulocytes, a measurement item related to nucleated red blood cells, a measurement item related to immature blood cells, and a measurement item related to abnormal lymphocytes; and wherein the second group comprises at least one of a measurement item relating to hematopoietic progenitor cells, and a measurement item relating to malaria parasite.

18. A blood cell analyzer with a first measurement mode, and a second measurement mode for measuring a second group of one or more measurement items in addition to a complete blood count measurement item and one or more measurement items of a first group that are measured in the first measurement mode, the blood cell analyzer comprising:

a sample aspirating section which comprises an aspiration tube for aspirating a blood sample, and which aspirates a blood sample from a sample container by using the aspiration tube;

a sample preparing section configured to prepare a measurement sample from the blood sample aspirated by the sample aspirating section and a reagent;

a measuring section configured to measure the measurement sample prepared by the sample preparing section; and an information processing unit configured to:

control the sample aspirating section so as to perform a first sample supplying operation in the first measurement mode, the first sample supplying operation comprises an operation of aspirating the blood sample by a first amount to only measure a complete blood count measurement item and the one or more measurement items of the first group and an operation of supplying the aspirated blood sample to the sample preparing section; and control the sample aspirating section so as to perform a second sample supplying operation and a third sample supplying operation in the second measurement mode, wherein the second sample supplying operation comprises an operation of aspirating the blood sample by the first amount for the complete blood count measurement item, and an operation of supplying the aspirated blood sample to the sample preparing section, and the third sample supplying operation comprises an operation of aspirating the blood sample by a second amount for the second group of one or more measurement items and an operation of supplying the aspirated blood sample to the sample preparing section, wherein the complete blood count measurement item comprises measuring the amount of red blood cells, platelets, hemoglobin, and white blood cells in the aspirated blood sample, wherein the first group comprises at least one of a white blood cell classification item for classifying white blood cells into a plurality of groups, a measurement item related to reticulocytes, a measurement item related to nucleated red blood cells, a measurement item related to immature blood cells, and a measurement item related to abnormal lymphocytes; and wherein the second group comprises at least one of a measurement item relating to hematopoietic progenitor cells, and a measurement item relating to malaria parasite.

\* \* \* \* \*

UNITED STATES PATENT AND TRADEMARK OFFICE
CERTIFICATE OF CORRECTION

PATENT NO. : 9,005,916 B2  
APPLICATION NO. : 13/729751  
DATED : April 14, 2015  
INVENTOR(S) : Masaharu Shibata Page 1 of 1

It is certified that error appears in the above-identified patent and that said Letters Patent is hereby corrected as shown below:

In the Claims

In column 26, claim 15, line 23, after "complete blood count" insert --measurement item--.

In column 27, claim 17, line 8, before "has been received" delete "instruction".

Signed and Sealed this
Twenty-third Day of February, 2016

Michelle K. Lee
*Director of the United States Patent and Trademark Office*